(12) United States Patent
Adams et al.

(10) Patent No.: US 6,288,062 B1
(45) Date of Patent: Sep. 11, 2001

(54) OXAZOLES FOR TREATING CYTOKINE MEDIATED DISEASES

(75) Inventors: Jerry Leroy Adams, Wayne; Timothy Francis Gallagher, Harleysville; Jeffrey Charles Boehm, King of Prussia; Susan Mary Thompson, Phoenixville, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/467,164

(22) Filed: Dec. 20, 1999

Related U.S. Application Data

(63) Continuation of application No. 08/640,966, filed as application No. PCT/US94/13067 on Nov. 8, 1994, now abandoned, which is a continuation-in-part of application No. 08/148,705, filed on Nov. 8, 1993.

(51) Int. Cl.[7] .................. A61K 3/535; C07D 421/00; C07D 417/00
(52) U.S. Cl. .................. 514/236.8; 514/236.8; 546/268.1; 546/268.4; 546/271.4
(58) Field of Search ............. 546/268.4, 271.1; 514/236.8

(56) References Cited

U.S. PATENT DOCUMENTS

| 4,447,431 | 5/1984 | Sallman | 424/246 |
|---|---|---|---|
| 5,254,576 | 10/1993 | Romine et al. | 514/365 |

FOREIGN PATENT DOCUMENTS

| 45081 | 2/1982 | (DE) . |
|---|---|---|
| 2 123 831 A | 2/1984 | (GB) . |

OTHER PUBLICATIONS

Sallmann, A., 100 (1): 6496W, 1983.
Sallmann, A., 99 (21): 175755W. 1983.
Sallmann, A., 99 (3): 22451U. 1982.
Sallmann, A., 97 (1): 6298C. 1982.
Sallmann, A., 97 (11): 92274W. 1982.
Sallmann, A., 83 (15): 131598N. 1985.
Chem Abstr, vol. 97, 6298, 1982.
Chem Abstr, vol. 97, No. 11, Sep. 13, 1982, abstract No. 92274w, EP 46,451 (Feb. 24, 1982).
Chem Abstr, vol. 83, No. 15, Oct. 13, 1975, abstract No. 131598n, Swiss 561,718 (May 15, 1975).

*Primary Examiner*—Sabiha Qazi
(74) *Attorney, Agent, or Firm*—Dara L. Dinner; Stephen Venetianer; Charles M. Kinzig

(57) ABSTRACT

This invention relates to the novel oxazole compounds of Formula (I) and novel pharmaceutical compositions comprising a compound of Formula (I) and a pharmaceutically acceptable diluent or carrier. This invention also relates to a method of inhibiting cytokines and the treatment of cytokine mediated diseases, in mammals, thereby by administration of an effective amount of a compound according to Formula (I).

16 Claims, No Drawings

OXAZOLES FOR TREATING CYTOKINE MEDIATED DISEASES

This application is a continuation of U.S. Ser. No. 08/640,966 filed May 8, 1996 which is the §371 national stage entry of PCT/US94/13067, filed Nov. 8, 1994 which is a continuation in part of U.S. Ser. No. 08/148,705 filed Nov. 8, 1993.

FIELD OF THE INVENTION

This invention relates to a novel group of oxazole compounds, processes for the preparation thereof, the use thereof in treating cytokine mediated diseases and pharmaceutical compositions for use in such therapy.

BACKGROUND OF THE INVENTION

Interleukin-1 (IL-1)and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., *Rev. Infect. Disease*, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes and pancreatic β cells.

Dinarello, *J. Clinical Immunology*, 5 (5), 287–297 (1985), reviews the biological activities which have been attributed to IL-1. It should be noted that some of these effects have been described by others as indirect effects of IL-1.

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T Cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Monokines, specifically TNF, are implicated in activated T-cell mediated HIV protein expression and/or virus replication by playing a role in maintaining T lymphocyte activation. Therefore, interference with monokine activity such as by inhibition of monokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T-cells, are targets for viral replication and the level of viral replication is dependent upon the activation state of the cells. [See Rosenberg et al., The Immunopathogenesis of HIV Infection, Advances in Immunology, Vol. 57, (1989)]. Monokines, such as TNF, have been shown to activate HIV replication in monocytes and/or macrophages [See Poli, et al., Proc. Natl. Acad. Sci., 87:782–784 (1990)], therefore, inhibition of monokine production or activity aids in limiting HIV progression as stated above for T-cells.

TNF has also been implicated in various roles with other viral infections, such as the cytomegalia virus (CMV), influenza virus, and the herpes virus for similar reasons as those noted.

Interleukin-8 (IL-8) is a chemotactic factor first identified and characterized in 1987. IL-8 is produced by several cell types including mononuclear cells, fibroblasts, endothelial cells, and keratinocytes. Its production from endothelial cells is induced by IL-1, TNF, or lipopolysachharide (LPS). Human IL-8 has been shown to act on Mouse, Guinea Pig, Rat, and Rabbit Neutrophils. Many different names have been applied to IL-8, such as neutrophil attractant/activation protein-1 (NAP-1), monocyte derived neutrophil chemotactic factor (MDNCF), neutrophil activating factor (NAF), and T-cell lymphocyte chemotactic factor.

IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD18) on neutrophils without de novo protein synthesis, this may contribute to increased adhesion of the neutrophils to vascular endothelial cells. Many diseases are characterized by massive neutrophil infiltration. Conditions associated with an increased in IL-8 production (which is responsible for chemotaxis of neutrophils into the inflammatory site) would benefit by compounds which are suppressive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

There remains a need for treatment, in this field, for compounds which are cytokine suppressive anti-inflammatory drugs, i.e. compounds which are capable of inhibiting cytokines, such as IL-1, IL-6, IL-8 and TNF.

SUMMARY OF THE INVENTION

This invention relates to the novel compounds of Formula (I) and pharmaceutical compositions comprising a compound of Formula (I) and a pharmaceutically acceptable diluent or carrier.

This invention also relates to a method of inhibiting cytokines and the treatment of a cytokine mediated disease, in a mammal in need thereof, which comprises administering to said mammal an effective amount of a compound of Formula (I).

This invention more specifically relates to a method of inhibiting the production of IL-1 in a mammal in need thereof which comprises administering to said mammal an effective amount of a compound of Formula (I).

This invention more specifically relates to a method of inhibiting the production of IL-8 in a mammal in need thereof which comprises administering to said mammal an effective amount of a compound of Formula (I).

This invention more specifically relates to a method of inhibiting the production of TNF in a mammal in need thereof which comprises administering to said mammal an effective amount of a compound of Formula (I).

DETAILED DESCRIPTION OF THE INVENTION

The novel compounds of this invention are represented by the structure:

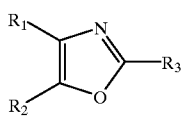

(I)

wherein:

$R_1$ and $R_2$ are independently selected from an optionally substituted aryl or heteroaryl group, provided that at least one of $R_1$ and $R_2$ is an optionally substituted heteroaryl, and further provided that both $R_1$ and $R_2$ are not the same heteroaryl group;

wherein when one of $R_1$ and $R_2$ is an optionally substituted aryl ring, the ring is substituted by one or two substituents, each of which is independently selected, and which, for a 4-phenyl, 4-naphth-1-yl or 5-naphth-2-yl substituent, is halo, cyano, —C(Z)$NR_7R_{17}$, —C(Z)$OR_{23}$, —$(CR_{10}R_{20})_m COR_{36}$, —$SR_5$, —$SOR_5$, —$OR_{36}$, halo-substituted-$C_{1-4}$ alkyl, $C_{1-4}$ alkyl, —ZC(Z)$R_{36}$, —$NR_{10}C(Z)R_{23}$, or —$(CR_{10}R_{20})_m NR_{10}R_{20}$;

and which, for other positions of substitution, is halo, —$(CR_{10}R_{20})_{m''}$-cyano, —C(Z)$NR_{16}R_{26}$, —C(Z) $OR_8$, —$(CR_{10}R_{20})_{m''}COR_8$, —$(CR_{10}R_{20})_{m''}S(O)_m R_8$, —$(CR_{10}R_{20})_{m''}OR_8$, halo-substituted-$C_{1-4}$ alkyl, —$C_{1-4}$ alkyl, —$(CR_{10}R_{20})_{m''}NR_{10}C(Z)R_8$, —$(CR_{10}R_{20})_{m''}NR_{10}S(O)_{m'}R_{11}$, —$(CR_{10}R_{20})_{m''}$ $NR_{10}S(O)_{m'}NR_7R_{17}$, —$(CR_{10}R_{20})_{m''}ZC(Z)R_8$ or —$(CR_{10}R_{20})_{m''}NR_{16}R_{26}$;

and when one of $R_1$ and $R_2$ is an optionally substituted heteroaryl group, the substituent groups include one or two substituents each of which is independently selected from $C_{1-4}$ alkyl, halo, $C_{1-4}$ alkoxy, $C_{1-4}$ alkylthio, $NR_{10}R_{20}$, or an N-heterocyclyl ring which ring has from 5 to 7 members and optionally contains an additional heteroatom selected from oxygen, sulfur or $NR_{22}$;

$R_3$ is —$X_a P(Z)(X_b R_{13})_2$, $X_c$ or —$(CR_{10}R_{20})_n R_4$;

$R_4$ is Q—$(Y_1)_t$;

Q is an aryl or heteroaryl group;

$X_c$ is hydrogen, —$(CR_{10}R_{20})_n(Y_2)_p$, —$(CR_{10}R_{20})_n$— C=C—$(CR_{10}R_{20})_n(Y_2)_p$, —$(CR_{10}R_{20})_n$—C≡C— $(CR_{10}R_{20})_{n'}(Y_2)_p$, or halosubstituted $C_{1-10}$ alkyl;

t is an integer having a value of 1 to 3;

p is 0 or an integer having a value of 1, provided that when p is 0 then $Y_2$ is hydrogen;

$X_a$ is —$NR_8$—, —O—, —S— or a $C_{1-10}$ alkylene chain optionally substituted by $C_{1-4}$ alkyl and optionally interrupted by —$NR_8$—, —O— or —S—;

$X_b$ is independently selected from —$(CR_{10}R_{20})_n$, —$NR_8$—, —O— or —S—;

Z is oxygen or sulfur;

n is 0 or an integer having a value of 1 to 10;

n' is an integer having a value of 1 to 10;

m is 0, or the integer 1 or 2;

m' is 1 or 2;

m" is 0 or an integer having a value of 1 to 5;

$Y_1$ is independently selected from hydrogen, $C_{1-5}$ alkyl, halo-substituted $C_{1-5}$ alkyl, halogen, —$X_a$—P(Z)— $(X_b R_{13})_2$ or —$(CR_{10}R_{20})_n Y_2$;

$Y_2$ is halogen, —$OR_8$, —$NO_2$, —$S(O)_{m'}R_{11}$, —$SR_8$, —$S(O)_m NR_8R_9$, —$NR_8R_9$, —$O(CR_{10}R_{20})_n NR_8R_9$, —$C(O)R_8$, —$CO_2R_8$, —$CO_2(CR_{10}R_{20})_n CONR_8R_9$, —$ZC(O)R_8$, —$CN$, —$C(Z)NR_8R_9$, —$NR_{10}C(Z)R_8$, —$C(Z)NR_8OR_9$, —$NR_{10}C(Z)NR_8R_9$, —$NR_{10}S(O)_m$ $R_{11}$, —$N(OR_{21})C(Z)NR_8R_9$, —$N(OR_{21})C(Z)R_8$, —$C(=NOR_{21})R_8$, —$NR_{10}C(=NR_{15})SR_{11}$, —$NR_{10}C$ $(=NR_{15})NR_8R_9$, —$NR_{10}C(=CR_{14}R_{24})SR_{11}$, —$NR_{10}C(=CR_{14}R_{24})NR_8R_9$, —$NR_{10}C(O)C(O)$ $NR_8R_9$, —$NR_{10}C(O)C(O)OR_{10}$, —$C(=NR_{13})NR_8R_9$, —$C(=NOR_{13})NR_8R_9$, —$C(=NR_{13})ZR_{11}$, —$OC(Z)$ $NR_8R_9$, —$NR_{10}S(O)_2 CF_3$, —$NR_{10}C(Z)OR_{10}$, 5-($R_{18}$)- 1,2,4-oxadizaol-3-yl or 4-($R_{12}$)-5-($R_{18}R_{19}$)-4,5- dihydro-1,2,4-oxadiazol-3-yl;

$R_5$ is hydrogen, $C_{1-4}$ alkyl, $C_{2-4}$ alkenyl, $C_{2-4}$ alkynyl or $NR_7R_{17}$, excluding the moieties —$SR_5$ being —$SNR_7R_{17}$ and —$SOR_5$ being —$SOH$;

$R_6$ is $C_{1-4}$ alkyl, halo-substituted-$C_{1-4}$ alkyl $C_{2-4}$ alkenyl, $C_{2-4}$ alkynyl or $C_{3-5}$ cycloalkyl;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{22}$;

$R_8$ is hydrogen, heterocyclyl, heterocyclylalkyl or $R_{11}$;

$R_9$ is hydrogen, $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl, heteroaryl or heteroarylalkyl or $R_8$ and $R_9$ may together with the nitrogen to which they are attached form a heterocyclic ring of 5 to 7 members which ring optionally contains an additional heteroatom selected from oxygen, sulfur or $NR_{12}$;

$R_{10}$ and $R_{20}$ is each independently selected from hydrogen or $C_{1-4}$ alkyl;

$R_{11}$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl, heteroaryl or heteroarylalkyl;

$R_{12}$ is hydrogen, —C(Z)$R_{13}$ or optionally substituted $C_{1-4}$ alkyl, optionally substituted aryl or optionally substituted aryl-$C_{1-4}$ alkyl;

$R_{13}$ is hydrogen, $C_{1-10}$ alkyl, cycloalkyl, heterocyclyl, aryl, arylalkyl, heteroaryl or heteroarylalkyl;

$R_{14}$ and $R_{24}$ is each independently selected from hydrogen, alkyl, nitro or cyano;

$R_{15}$ is hydrogen, cyano, $C_{1-4}$ alkyl, $C_{3-7}$ cycloalkyl or aryl;

$R_{16}$ and $R_{26}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_{12}$;

$R_{18}$ and $R_{19}$ is each independently selected from hydrogen, $C_{1-4}$ alkyl, substituted alkyl, optionally substituted aryl, optionally substituted arylalkyl or together $R_{18}$ and $R_{19}$ denote a oxygen or sulfur;

$R_{21}$ is hydrogen, a pharmaceutically acceptable cation, $C_{1-10}$ alkyl, $C_{3-7}$ cycloalkyl, aryl, aryl $C_{1-4}$ alkyl, heteroaryl, heteroarylalkyl, heterocyclyl, aroyl, or $C_{1-10}$ alkanoyl;

$R_{22}$ is $R_{10}$ or $C(Z)$—$C_{1-4}$ alkyl;

$R_{23}$ is $C_{1-4}$ alkyl, halo-substituted-$C_{1-4}$ alkyl, or $C_{3-5}$ cycloalkyl;

$R_{36}$ is hydrogen or $R_{23}$;

or a pharmaceutically acceptable salt thereof.

Suitable heteroaryl moieties for $R_1$ and $R_2$ are 4-pyridyl, pyrimidinyl, quinolyl, isoquinolinyl, 1-imidazolyl, 1-benzimidazolyl and thiophene, all of which may be optionally substituted. Preferably, the heteroaryl group is a 4-pyridyl, 4-pyrimidinyl, 4-quinolyl, 6-isoquinolinyl, 1-imidazolyl or 1-benzimidazolyl group, of which the 4-pyridyl, 4-pyrimidinyl and 4-quinolyl is more preferred. Especially preferred is the 4-pyridyl or 4-pyrimidinyl moiety, and most preferred is the 4-pyrimidinyl moiety.

Suitable substituent groups for the heteroaryl moieties, $R_1$ and $R_2$, include one or two substituents each of which are independently selected from $C_{1-4}$ alkyl, halo, $C_{1-4}$ alkoxy, $C_{1-4}$ alkylthio, $NR_{10}R_{20}$ or an N-heterocyclyl ring which ring has from 5 to 7 members and optionally contains an additional heteroatom selected from oxygen, sulfur or $NR_{22}$.

A preferred substituent for the heteroaryl moieties is $C_{1-4}$ alkyl or $NR_{10}R_{20}$, more preferably $NR_{10}R_{20}$. Preferably, when the substituent is $C_{1-4}$ alkyl group it is methyl. When the substituent is $NR_{10}R_{20}$, and $R_{10}$ and $R_{20}$ are a $C_{1-4}$ alkyl moiety, it is preferably a methyl group, and more preferably $R_{10}$ and $R_{20}$ are not both $C_{1-4}$ alkyl groups. More preferably, both $R_{10}$ and $R_{20}$ are hydrogen or one of $R_{10}$ and $R_{20}$ are hydrogen and the other a C1-4 alkyl group, especially methyl. Preferably, the 4-pyridyl group is substituted in the 2-position and the 4-pyrimidinyl group is substituted at the 2- or 4-position, more preferably the 2-position (between the two nitrogen's of the pyrimidine ring.

For the purposes herein the "core" 4-pyrimidinyl moiety is meant to be the formula:

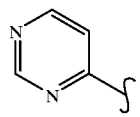

When the 4-pyrimidinyl moiety is substituted it is preferably substituted in at least one of the following positions by the moiety $Y_3$ and $Y_4$ which are referred to herein in greater detail as optional substituents on the heteroaryl rings $R_1$ and $R_2$:

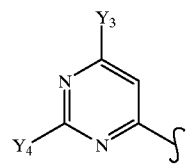

As the nomenclature will change when either $Y_3$ or $Y_4$ is substituted, for the purposes herein when $Y_4$ but not $Y_3$ is the substituted position it is referred to as the 2-position. When $Y_3$ but not $Y_4$ is the substituted position it is referred to as the 4-position and the point of attachment of the pyrimidinyl ring is the 6-position.

Suitable aryl groups for $R_1$ and $R_2$ include optionally substituted phenyl, naphth-1-yl or naphth-2-yl. The aryl ring may be optionally substituted by one or two substituents, each of which is independently selected, and which, for a 4-phenyl, 4-naphth-1-yl or 5-naphth-2-yl substituent, is halo, cyano, —C(Z)$NR_7R_{17}$, —C(Z)$OR_{23}$, —(C$R_{10}R_{20}$)$_m$·$COR_{36}$, —$SR_5$, —$SOR_5$, —$OR_{36}$, halo-substituted-$C_{1-4}$ alkyl, $C_{1-4}$ alkyl, —$ZC(Z)R_{36}$, —$NR_{10}C(Z)R_{23}$, or —(C$R_{10}R_{20}$)$_m$·$NR_{10}R_{20}$ and which, for other positions of substitution, is halo, (C$R_{10}R_{20}$)$_m$··cyano, —C(Z)$NR_{16}R_{26}$, —C(Z)$OR_8$, —(C$R_{10}R_{20}$)$_m$··$COR_8$, (C$R_{10}R_{20}$)$_m$··$S(O)_mR_8$, (C$R_{10}R_{20}$)$_m$··$OR_8$, halo-substituted-$C_{1-4}$ alkyl, $C_{1-4}$ alkyl, —(C$R_{10}R_{20}$)$_m$··$NR_{10}C(Z)R_8$, (C$R_{10}R_{20}$)$_m$··$NR_{10}S(O)_mR_{11}$, (C$R_{10}R_{20}$)$_m$··$NR_{10}S(O)_mNR_7R_{17}$, (C$R_{10}R_{20}$)$_m$··$ZC(Z)R_8$ or —(C$R_{10}R_{20}$)$_m$··$NR_{16}R_{26}$;

n is 0 or an integer having a value of 1 to 10; n' is an integer having a value of 1 to 10; m is 0, or the integer 1 or 2; m' is 1 or 2; and m" is 0 or an integer having a value of 1 to 5.

Preferred substitutions for $R_1$ or $R_2$ when it is a 4-phenyl, 4-naphth-1-yl or 5-naphth-2-yl moiety are one or two substituents each independently selected from halogen, —$SR_5$, —$SOR_5$, —$OR_{36}$, or —(C$R_{10}R_{20}$)$_m$$NR_{10}R_{20}$, and for other positions of substitution on these rings preferred substitution is halogen, —S(O)$_mR_8$, —$OR_8$, —(C$R_{10}R_{20}$)$_m$··$NR_7R_{17}$, (C$R_{10}R_{20}$)$_m$··$NR_{10}C(Z)R_8$ and —(C$R_{10}R_{20}$)$_m$··$NR_{10}S(O)_m$·$R_{11}$. More preferred substituents for the 4-position in phenyl and naphth-1-yl and on the 5-position in naphth-2-yl include halogen, especially fluoro and chloro, and —$SR_5$ and —$SOR_5$ wherein $R_5$ is preferably a $C_{1-2}$ alkyl, more preferably methyl; of which halogen, especially fluoro is preferred. Preferred substituents for the 3-position in phenyl and naphth-1-yl include: halogen, especially chloro; —$OR_8$, especially $C_{1-4}$ alkoxy; amino; —$NR_{10}C(Z)R_8$, especially —NHCO($C_{1-10}$ alkyl); and —$NR_{10}S(O)_m$·$R_{11}$, especially —NHS(O)$_2$($C_{1-10}$ alkyl).

Preferably, the aryl group is an unsubstituted or substituted phenyl moiety. More preferably, it is phenyl or phenyl substituted at the 4-position with fluoro and/or substituted at the 3-position with fluoro, chloro, $C_{1-4}$ alloxy, methanesulfonamido or acetamido.

Preferably when one of $R_1$ or $R_2$ is the heteroaryl group, $R_2$ is the heteroaryl position.

Suitably, $R_3$ is —$X_c$ or (C$R_{10}R_{20}$)$_nR_4$. When $R_3$ is —$X_c$ it is preferably hydrogen, (C$R_{10}R_{20}$)$_nCH_3$, or (C$R_{10}R_{20}$)$_nY_2$. More preferably, $Y_2$ includes —$NR_8R_9$, and —$NR_{10}C(Z)R_8$ and n is 0 to 2. Most preferably, $R_3$ is hydrogen, methyl, amino, or acetamido.

Suitably, when $R_3$ is —(C$R_{10}R_{20}$)$_nR_4$, and Q is an aryl group, then it is preferably an optionally substituted phenyl, or if Q is a heteroaryl group it is preferably a (un)substituted pyrrole, pyridine, or pyrimidine group. More preferably Q is phenyl or a substituted phenyl. All Q moieties are independently substituted by ($Y_1$)$_t$, wherein t is an integer of 1 to 3. Preferably t is 1 or 2. More preferably, when $R_3$ is monosubstituted phenyl (t=1), the substituent is located at the 4-position. The n term is preferably 0 to 2.

Suitably, when $R_4$ is Q—$(Y_1)t$ and when $Y_1$ is other than $(CR_{10}R_{20})_nY_2$, preferred substituents include hydrogen, halogen, or $C_{1-5}$ alky. When $Y_1$ is $(CR_{10}R_{20})_nY_2$ and Q is mono-substituted the substituents include —$(CR_{10}R_{20})_nY_2$ wherein: n is 0, 1, 2 or 3, preferably 0 or 1; and $Y_2$ is —$OR_8$, especially where $R_8$ is hydrogen or $C_{1-10}$ alkyl; —$NO_2$; —$S(O)_{m'}R_{11}$, especially where $R_{11}$ is $C_{1-10}$ alkyl; —$SR_8$, especially where $R_8$ is $C_{1-10}$ alkyl; —$S(O)_mNR_8R_9$, especially where $R_8$ and $R_9$ is each hydrogen or $C_{1-10}$ alkyl or $R_8$ and $R_9$ together with the nitrogen to which they are attached form a 5 to 7 membered ring which optionally includes another heteroatom selected from oxygen, sulfur or $NR_{12}$; —$NR_8R_9$, especially where $R_8$ and $R_9$ is each hydrogen, methyl or benzyl or $R_8$ and $R_9$ together with the nitrogen to which they are attached form a 5 to 7 membered ring which optionally includes another heteroatom selected from oxygen, sulfur or $NR_{12}$; —$O(CR_{10}R_{20})_nNR_8R_9$, especially where $R_8$ and $R_9$ is each $C_{1-10}$ alkyl; —$C(O)R_8$, especially where $R_8$ is hydrogen or $C_{1-10}$ alkyl; —$CO_2R_8$, especially where $R_8$ is hydrogen or $C_{1-10}$ alkyl; —$CO_2(CR_{10}R_{20})_{n'}CONR_8R_9$, especially where $R_8$ and $R_9$ is hydrogen or $C_{1-10}$ alkyl; —CN; —$C(Z)NR_8R_9$, especially where $R_8$ and $R_9$ is hydrogen or $C_{1-10}$ alkyl; —$NR_{10}S(O)_{m'R11}$, especially where $R_{10}$ is hydrogen or $C_{1-10}$ alkyl and $R_{11}$ is $C_{1-10}$ alkyl or a halosubstituted; —$NR_{10}C(Z)R_8$, especially where $R_8$ is $C_{1-10}$ alkyl and $R_{10}$ is hydrogen and Z is oxygen; —$C(Z)NR_8OR_9$, especially where $R_8$ and $R_9$ is each hydrogen and Z is oxygen; —$NR_{10}C(Z)NR_8R_9$, especially where $R_8$ and $R_9$ is each hydrogen or $C_{1-10}$ alkyl and Z is oxygen; —$N(OR_{21})C(Z)NR_8RR_9$, especially where $R_8$ especially where $R_8$, $R_9$ and $R_{21}$ is each hydrogen or $C_{1-10}$ alkyl and Z is oxygen; —$C(=NOR_{13})NR_8R_9$, especially where $R_8$, $R_9$ and $R_{13}$ is each hydrogen; —$NR_{10}C(=NR_{15})NR_8R_9$, especially where $R_8$ and $R_9$ is hydrogen, $C_{1-10}$ alkyl or arylalkyl and $R_{15}$ is cyano; and 5-$(R_{18})$-1,2,4-oxadizaol-3-yl and 4-$(R_{12})$-5-$(R_{18}R_{19})$-4,5-dihydro-1,2,4-oxadiazol-3-yl, especially where $R_{12}$ is hydrogen and $R_{18}$ and $R_{19}$ is each hydrogen or $C_{1-10}$ alkyl or together are oxo.

More preferably, when $Y_1$ is $(CR_{10}R_{20})_nY_2$, n is 0 to 2 and $Y_2$ is —$OR_8$, especially where $R_8$ is $C_{1-10}$ alkyl; —$S(O)_{m'}R_{11}$, especially where $R_{11}$ is $C_{1-10}$ alkyl; —$SR_8$, especially where $R_8$ is $C_{1-10}$ alkyl; —$NR_8R_9$, especially where $R_8$ and $R_9$ is hydrogen, alkyl, aryl alkyl, or aryl or $R_8$ and $R_9$ together with the nitrogen to which they are attached form a pyrrolidinyl, piperidinyl or morpholinyl ring, more preferably the $R_8$ and $R_9$ terms in the $NR_8R_9$ moiety are hydrogen, methyl or benzyl; —$CO_2R_8$, especially where $R_8$ is hydrogen or $C_{1-10}$ alkyl; —$S(O)_mNR_8R_9$, especially where $R_8$ and $R_9$ is each hydrogen or $C_{1-10}$ alkyl; —$NR_{10}S(O)_mR_{11}$, especially where $R_{10}$ is hydrogen and $R_{11}$ is $C_{1-10}$ alkyl or 5-$(R_{18})$-1,2,4-oxadizaol-3-yl and 4-$(R_{12})$-5-$(R_{18}R_{19})$-4,5-dihydro-1,2,4-oxadiazol-3-yl, especially where $R_{12}$ is hydrogen and $R_{18}$ and $R_{19}$ is hydrogen or $C_{1-10}$ alkyl or together are oxo.

Most preferably, when $Y_1$ is $(CR_{10}R_{20})_nY_2$, n is 0 to 2 and $Y_2$ is —$OR_8$, especially where $R_8$ is $C_{1-4}$; —$S(O)_{m'}R_{11}$, especially where $R_{11}$ is $C_{1-4}$ alkyl; —$SR_8$, especially where $R_8$ is $C_{1-4}$ alkyl; —$NR_8R_9$, especially where $R_8$ and $R_9$ is hydrogen, $C_{1-4}$ alkyl, phenyl $C_{1-4}$ alkyl, or phenyl or $R_8$ and $R_9$ together with the nitrogen to which they are attached form a pyrrolidinyl, piperidinyl or morpholinyl ring, more preferably the $R_8$ and $R_9$ terms in the $NR_8R_9$ moiety are hydrogen, methyl or benzyl. Specific embodiments of minosubstituted phenyls, prefereably at the 4-position, are $C_{1-10}$ alkylthio, $C_{1-10}$ alkylsulfinyl, $C_{1-10}$ alkylsulfonyl, N,N-di$(C_{1-10}$ alkyl)amino $C_{1-2}$ alkyl, N-aralkyl-N—$C_{1-10}$ alkylamino $C_{1-2}$ alkyl, N-morpholino $C_{1-2}$ alkyl $C_{1-10}$ alkylsulfonamido, sulphonamido $C_{1-2}$ alkyl, 5-$C_{1-10}$ alkyl-4,5-dihydro-1,2,4-oxadiazol-3-yl or 5,5-di$(C_{1-10}$ alkyl)-4,5-dihydro-1,2,4 -oxadiazol-3-yl. More preferably susbtituted with $C_{1-4}$ alkylthio, $C_{1-4}$ alkylsulfinyl, or $C_{1-4}$ alkylsulfonyl and most preferably the $C_{1-4}$ alkyl is methyl.

Preferred substituents for use in $R_3$ when the aryl or heteroaryl group Q is disubstituted include those hereinbefore listed for use when Q is mono-substituted and, as further substituent(s), halogen and $C_{1-10}$ alkyl. When Q is phenyl substituted with two or three substituents, the alkyl moieties preferably have from one to three carbons, more preferably one. Preferred ring positions for two substituents are the 3- and 4-positions, and, for three substituents, the 3-, 4- and 5- positions. The substituent at the 3- and 5-positions is preferably $C_{1-2}$ alkyl, such as methyl, or halogen, such as bromo, fluoro or chloro, while the substituent at the 4-position is preferably hydroxyl.

In all instances herein where there is an alkenyl or alkynyl moiety as a substituent group, such as in $R_5$, $R_8$, $R_9$, or $R_{11}$ the unsaturated linkage, ie., the vinylene or acetylene linkage is preferably not directly attached to the nitrogen, oxygen or sulfur moieties, for instance in $Y_2$ as C(Z)$NR_8OR_9$, $NR_{10}C(Z)NR_8RR_9$, or $OR_8$.

As used herein, "optionally substituted" unless specified, refers to such groups as halogen, hydroxyl, alkoxy, $S(O)_m$ $C_{1-6}$ alkyl amino, a mono & di-substituted amino, such as an $NR_7R_{17}$ group, $C_{1-6}$ alkyl, halo substituted $C_{1-6}$ alky, $C_{3-7}$ cycloalkyl, an optionally substituted aryl or an optionally substituted arylalkyl wherein the substituents are halogen, hydroxyl, alkoxy, $S(O)_mC_{1-6}$ alkyl, amino, a mono & di-substituted amino, such as an $NR_7R_{17}$ group, $C_{1-6}$ alkyl, or halo substituted $C_{1-6}$ alkyl, unless otherwise specified herein.

When $R_3$ includes a $X_a$—$P(Z)(X_bR_{13})_2$ group linked either directly to the oxazole ring or indirectly via an aryl or heteroaryl group, $X_a$ is suitably oxygen or $C_{1-4}$ alkylene, optionally interrupted by oxygen, for instance —$CH_2OCH_2$— and Z and $X_b$ is each oxygen, such that the preferred groups include —$OP(O)(OR_{13})_2$ and —$CH_2OCH_2$—$P(O)(OR_{13})_2$.

In a preferred subgenus of compounds of formula (I), one of $R_1$ or $R_2$ is 4-pyridyl, 2-alkyl-4pyridyl, 2-$NR_{10}R_{20}$-4-pyridyl, 4-pyrimidinyl, 2-alkyl-pyrimidin-4-yl, 2-$NR_{10}R_{20}$-pyrimidin-4-yl, 4-$NR_{10}R_{20}$pyrimidin-6-yl, or 4-quinolyl. Preferably $R_3$ is hydrogen, methyl, amino, or acetamido or phenyl or phenyl substituted with a substituent selected from —$(CR_{10}R_{20})_nY_2$ wherein n is 0, 1, 2 or 3 and $Y_2$ is —$OR_8$, —$NO_2$, —$S(O)_mR_{11}$, —$SR_8$, —$S(O)_mNR_8R_9$, —$NR_8NR_9$, —$O(CR_{10}R_{20})_nNR_8R_9$, —$C(O)R_8$, —$CO_2R_8$, —$CO_2R_8$, —$CO_2(CR_{10}R_{20})_nCONR_8R_9$, —CN, —$C(Z)NR_8R_9$, —$C(Z)NR_8OR_9$, —$NR_{10}S(O)_mR_{11}$, —$NR_{10}C(Z)R_8$, —$NR_{10}C(Z)NR_8R_9$, —$C(=NOR_{13})NR_8R_9$, —$NR_{10}C$ $(=CR_{14}R_{24})NR_8R_9$, 5$(R_{18})$-1,2,4-oxadiazol-3-yl, 4-$(R_{12})$-5-$(R_{18}R_{19})$-4,5-dihydro-1,2,4-oxadiazol-3-yl, a 3,5-dimethyl or dibromo-4-hydroxyl grouping, wherein the substiutent is preferably at the 4-position; and the other of one of $R_1$ or $R_2$ is phenyl or phenyl substituted by fluoro, chloro, $C_{1-4}$ alkoxy, $S(O)_m$ $C_{1-4}$ alkyl, methanesulfonamido or acetamido. Preferably $R_1$ is the optionally substituted phenyl. More preferably $R_3$ is hydrogen, methyl, amino, or acetamido or phenyl substituted at the 4-position with $C_{1-10}$ alkyilthio, $C_{1-10}$ alkylsulfinyl, $C_{1-10}$ alkylsulfonyl.

In a more preferred subgenus $R_3$ is hydrogen, methyl, amino, or acetamido or phenyl substituted at the 4-position with $C_{1-10}$ alkylthio, $C_{1-10}$ alkylsulfinyl, $C_{1-10}$ alkylsulfonyl; and one of $R_1$ or $R_2$ is phenyl or phenyl substituted at the 4-position with fluoro and/or substituted at the 3-position with fluoro; chloro, $C_{1-4}$ alkoxy, methane-sulfonamido or acetamido; and the other of $R_1$ or $R_2$ is 4-pyridyl, 2-alkyl-4-pyridyl, 2—$NR_{10}R_{20}$-4-pyridyl, 4-pyrimidinyl, 2-alkyl-pyrimidin-4-yl, 2-$NR_{10}R_{20}$-pyrimidin-4yl, 4$NR_{10}R_{20}$-pyrimidin-6-yl, or 4-quinolyl. More preferably one of $R_1$ or $R_2$ is an $NR_{10}R_{20}$ substituted pyrimidinyl and most preferably it is the $R_2$ moiety.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of formula (I) may also be formed with a pharmaceutically acceptable cation, for instance, if a substituent $Y_1$ in $R_3$ comprises a carboxy group. Suitable pharmaceutically acceptable cations are well known to those skilled in the art and include alkaline, alkaline earth, ammonium and quarternary ammonium cations.

The following terms, as used herein, refer to:

"halo"—all halogens, that is chloro, fluoro, bromo and iodo;

"$C_{1-10}$alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, and the like;

The term "cycloalkyl" is used herein to mean cyclic radicals, preferably of 3 to 7 carbons, including but not limited to cyclopropyl, cyclopentyl, cyclohexyl, and the like;

The term "alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like;

"aryl"—phenyl and naphthyl;

"heteroaryl"(on its own or in any combination, such as "heteroaryloxy")—a 5–10 membered aromatic ring system in which one or more rings contain one or more heteroatoms selected from the group consisting of N, O or S, such as, but not limited, to pyrrole, thiophene, quinoline, isoquinoline, pyridine, pyrimidine, oxazole, thiazole, thiadiazole, triazole, imidazole, or benzimidazole;

"heterocyclic"(on its own or in any combination, such as "heterocyclylalkyl")—a saturated or wholly or partially unsaturated 4–10 membered ring system in which one or more rings contain one or more heteroatoms selected from the group consisting of N, O, or S; such as, but not limited to, pyrrolidine, piperidine, piperazine, morpholine, imidazolidine or pyrazolidine;

The term "aralkyl" or "heteroarylalkyl" or "heterocyclicalkyl" is used herein to mean $C_{1-4}$ alkyl as defined above unless otherwise indicated;

"aroyl"—a C(O)Ar, wherein Ar is as phenyl, napthyl, or aryl alkyl derivatives, such as benzyl and the like;

"alkanoyl"—a C(O)$C_{1-10}$alkyl wherein the alkyl is as defined above;

"sulfinyl"—the oxide S(O) of the corresponding sulfide while the term "thio" refers to the sulfide.

The compounds of the-present invention may contain one or more asymmetric carbon atoms and may exist in racemic and optically active forms. All of these compounds are included within the scope of the present invention.

Exemplified compounds of formula (I) include:
5-(3-Methoxyphenyl)-2-methyl-4-(4pyridyl)oxazole;
5-(4-Fluorophenyl)-2-methyl-4-(4-pyridyl)oxazole;
4-(4-Fluorophenyl)-5-(4-pyridyl)oxazole;
4-(3-Chlorophenyl)-5-(4-pyridyl)oxazole;
2-Amino-4-(4-fluorophenyl)-5-(4-pyridyl)oxazole;
2-Dimethylamino-4-(4-fluorophenyl)-5-(4-pyridyl)oxazole;
4-(4-Fluorophenyl)-5-(4-pyrimidinyl)oxazole;
4-(4-Fluorophenyl)-5-(2-aminopyrimidin-4-yl)oxazole;
4-(4-Fluorophenyl)-5-(2-methylaminopyrimidin-4-yl) oxazole;
4-(4-Fluorophenyl)-5-(2-dimethylaminopyrimidin-4-yl) oxazole;
4-(4-Fluorophenyl)-5-(2-methylthiopyrimidin-4-yl)oxazole;
4-(3-Chlorophenyl)-5-(2-methylpyrid-4-yl)oxazole;
4-(4-Fluorophenyl)-2-methyl-5-(4-pyridyl)oxazole;
4-(4-Fluorophenyl)-2-methyl-5-(4-quinolyl)oxazole;
5-(4-Fluorophenyl)-4-(2-aminopyrimidin-4-yl)oxazole;
2-Amino-5-(4-fluorophenyl)-4-(4-pyridyl)oxazole; and
2-Dimethylamino-5-(4-fluorophenyl)-4-(4-pyridyl)oxazole.

Preferred compounds of formula (I) include:
5-(3-Methoxyphenyl)-2-methyl-4-(4-pyridyl)oxazole;
5-(4-Fluorophenyl)-2-methyl-4(4-pyridyl)oxazole;
2-Methyl-4-(Phenyl)-5-(4-pyridyl)oxazole;
4-(4-Fluorophenyl)-2-methyl-5-(4-pyridyl)oxazole;
4-(4-Fluorophenyl)-2-phenyl-5-(4-pyridyl)oxazole;
2-Amino-4-(4-fluorophenyl)-5-(4-pyridyl)oxazole.
4-(4-Fluorophenyl)-5-(4-pyridyl)oxazole;
4-(4-Fluorophenyl)-5-(2-methylpyrid-4-yl)oxazole;
4-(3,4-Dichlorophenyl)-5-(4-pyridyl)oxazole;
4-(3-Chlorophenyl)-5-(4-pyridyl)oxazole;
4-(4-Fluorophenyl)-2-(4methylthiophenyl)-5-(4-pyridyl) oxazole;.
4-(4-Fluorophenyl)-2-[4-(methylsulfinyl)phenyl]-5-(4-pyridyl)oxazole;
4-(4Fluorophenyl)-5-(2-aminopyrimidin-4-yl)oxazole; and
2-Acetamido-4-(4-fluorophenyl)-5-(4-pyridyl)oxazole.

Compounds of Formula (I) are oxazole derivatives which may be readily prepared using procedures well known to those of skill in the art and may be prepared by analagous methods to those indicated herein below.

Scheme I

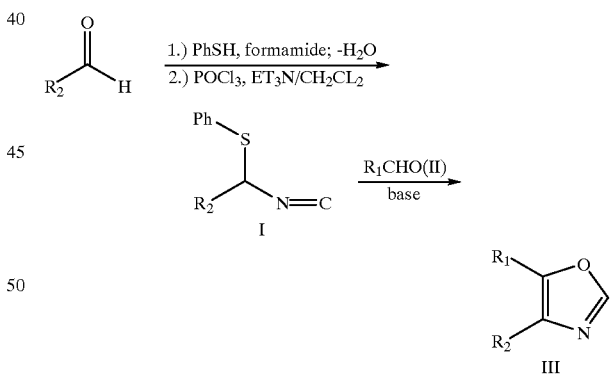

Scheme I illustrates the preparation of oxazoles which are substituted only by a hydrogen at C-2 ($R_3$=H). The requisite aldehydes wherein $R_2$ and $R_1$ are defined as in formula (I) or suitably protected precursors thereof can be prepared from readily available materials using standard transformations known to one skilled in the art The isonitrile (I) is prepared from an aldehyde ($R_2$COH), formamide and a thiol or a sulfinic acid (preferably as aryl compounds) in a 3 component condensation. For a more detailed description see Example 7 herein. Reaction of I with aldehyde II is initiated with a suitable base, for example a guanidine base such as 1,5,7 triazobicyclo[4.4.0]dec-5-ene, in an inert solvent such as methylene chloride or DME yields oxazole III.

Scheme II

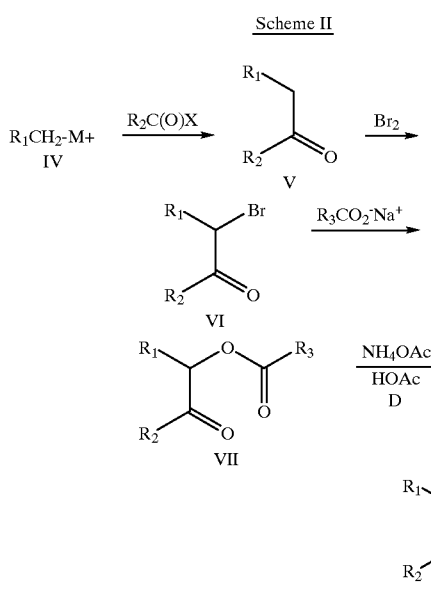

Scheme II illustrates the preparation of oxazoles possessing an alkyl group at C-2 (VIII) by cyclization of an appropriate acyloxyketone VII with $NH_4OAc/HOAc$. Compound VII can be prepared as illustrated in three steps from the desired organometalic derivative IV. A relevant example of the first step, preparation of ketone V, is outlined in Scheme II of PCT/US93/00674, Adams et al., published as WO93/14081 whose disclosure is incorporated by reference herein in its entirety. Compound V can be brominated to afford bromoketone VI. Displacement of the bromide by the sodium salt of a carboxylic acid gives acyloxyketone VII.

or employing basic conditions in alcoholic solvents with an alkyl nitrite, for example, potassium t-butoxide in t-butanol plus amyl nitrite. Subsequent reduction of the oximinoketone IX, preferably with hydrogen and a metal catalyst yields an aminoketone which may be prepared and isolated under acidic conditions to afford initially the hydrohalide salt which is in a separate step acylated to produce compound XI or acylated in situ to yield directly compound XI. In the other method, the corresponding oxime (X) of V can be converted, via a Neber reaction, to an aminoketone which after acylation affords XI. The third method produces XI by the addition of an organomettalic derivative of $R_2$ to the acylated and activated derivative of the α-amino acid of $R_1$.

Scheme IV

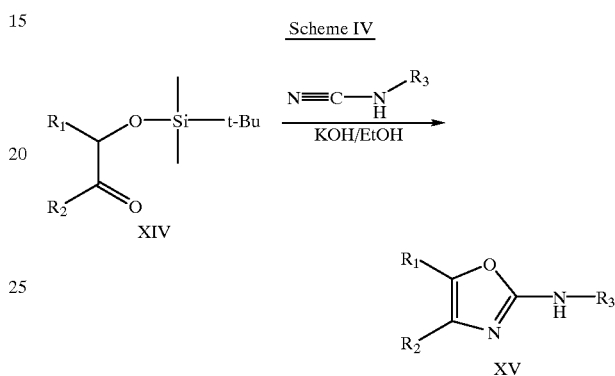

Scheme IV illustrates the preparation of 2-aminooxazoles XV. They can be prepared from silyloxyketone XIV and the desired cyanamide using the procedure described by Cockerill, A. F., et al, *Syn.*, 1976, 591. The preparation of compound XIV is outlined in Scheme I of Adams et al., PCT/US93/00674, supra.

Scheme III

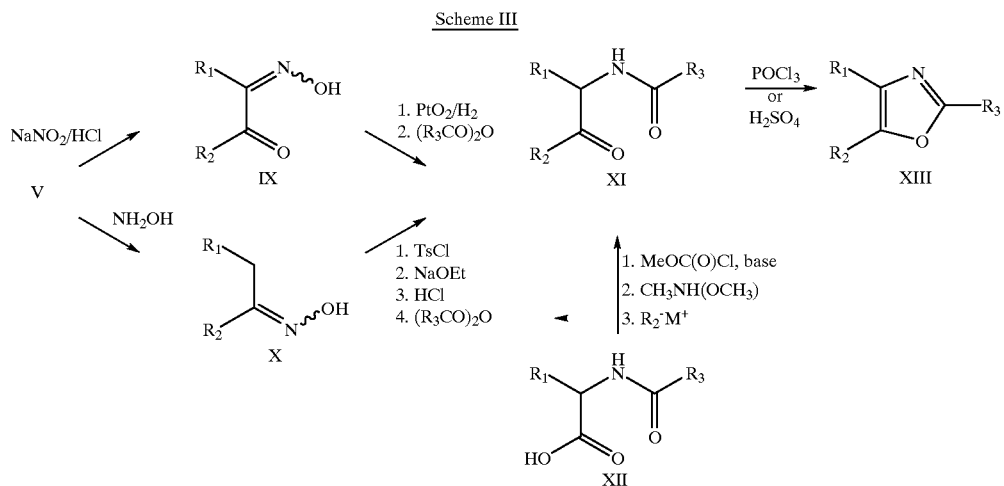

Scheme III illustrates an alternative route to the preparation of oxazoles possessing an alkyl substituent at C-2 (XIII). The procedure involves cyclizing the appropriate acylaminoketone XI under dehydrating conditions. Three methods of preparing compound XI are shown. Two of the methods start with ketone V. In one method, compound V can be converted to the oximinoketone IX using either acidic conditions with an aqueous solution of an alkali nitrite salt

Scheme V

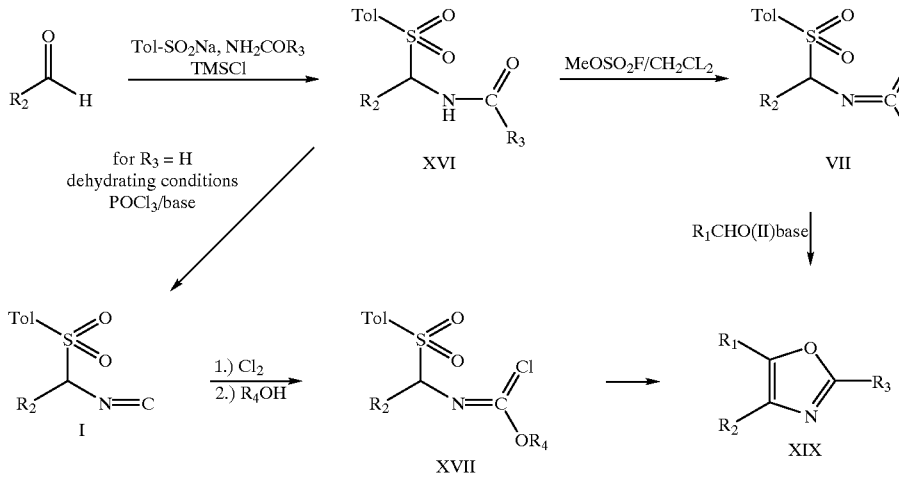

The route illustrated in Scheme V allows for the preparation of 2-substituted oxzaoles in which the $R_3$ group can be either the direct attachment of a carbon (alkyl or aryl) or an oxygen or sulfur heteroatom linker. The synthesis of the tosyl amides (XVI) and subsequent dehydration to the isonitrile (I) is analogous to that outlined in Scheme I, but yields products with the sulfur leaving group at the sulfone instead of sulfide oxidation state. Either oxidation state of sulfur is applicable to the processes outlined in Schemes I and V. Alkylation of the amide XVI on oxygen or sulfur if a thioamide is used) using an oxonium salt or under other conditions known to favor heteroatom versus carbon alkylation yields the imine XVII. Reaction of XVII with aldehyde II under the basic conditions required to initiate cycloaddition produces the oxazole XIX. Alternatively, the isonitrile I may be used to prepare chloroimidates (XVIII) which also undergo the based-induced cyclization with aldehyde II. Experimental procedures for the cyclization to the oxazole and the preparation of the intermediates are outlined in the following articles: A. M. van Leuson et al. in *Tet, Let.*, p143 (1976); *J. Heterocyclic Chem.*, 18, p1127 & p1133 (1981) whose disclosure is incorporated by reference herein in its entirety.

Once the oxazole nucleus has been established, further compounds of formula (I) may be prepared by applying standard techniques for functional group interconversion, for instance: —$C(O)NR_8R_9$ from —$CO_2CH_3$ by heating with or without catalytic metal cyanide, e.g. NaCN, and $HNR_8R_9$ in $CH_3OH$; —$OC(O)R_8$ from —OH with e.g., $ClC(O)R_8$ in pyridine; —$NR_{10}$—$C(S)NR_8R_9$ from —$NHR_{10}$ with an alkylisothiocyante or thiocyanic acid; $NR_6C(O)OR_6$ from —$NHR_6$ with the alkyl chloroformate; —$NR_{10}C(O)NR_8R_9$ from —$NHR_{10}$ by treatment with an isocyanate, e.g. HN=C=O or $R_{10}N$=C=O; —$NR_{10}$—C(O)$R_8$ from —$NHR_{10}$ by treatment with Cl—$C(O)R_8$ in pyridine; —$C(=NR_{10})NR_8R_9$ from —$C(NR_8R_9)SR_8$ with $H_3NR8^+OAc$—by heating in alcohol; —$C(NR_8R_9)SR_8$ from —$C(S)NR_8R_9$ with $R_6$-I in an inert solvent, e.g. acetone; —$C(S)NR_8R_9$ (where $R_8$ or $R_9$ is not hydrogen) from —$C(S)NH_2$ with $HNR_8R_9$, —C(=NCN)—$NR_8R_9$ from —$C(=NR_8R_9)$—$SR_8$ with $NH_2CN$ by heating in anhydrous alcohol, alternatively from —C(=NH)—$NR_8R_9$ by treatment with BrCN and NaOEt in EtOH; —$NR_{10}$—C(=NCN) $SR_8$ from —$NHR_{10}$ by treatment with $(R_8S)_2C$=NCN; —$NR_{10}SO_2R_8$ from —$NHR_{10}$ by treatment with $ClSO_2R_8$ by heating in pyridine; —$NR_{10}C(S)R_8$ from —$NR_{10}C(O)R_8$ by treatment with Lawesson's reagent [2,4-bis(4-methoxyphenyl)-1,3,2,4-dithiadiphosphetane-2,4-disulfide]; —$NR_{10}SO_2CF_3$ from —$NHR_6$ with triflic anhydride and base; —$NR_{10}C(O)$—C(O)—$OR_8$ from —$NHR_{10}$ with, e.g. methyloxalyl chloride and a base such as triethylamine; —$NR_{10}C(O)$—C(O)—$NR_8R_9$ from —$NR_{10}C(O)$—C(O)—$OR_8$ with $HNR_8R_9$; and 1—($NR_{10}$)—2-imidazolyl from —C(=NH)$NHR_{10}$ by heating with 2-chloroacetaldehyde in chloroform (wherein $R_6$, $R_8$, $R_9$ and $R_{10}$ are as hereinbefore defined).

Suitable protecting groups for use with hydroxyl groups, for instance, are well known in the art and described in many references, for instance, Protecting Groups in Organic Synthesis, Greene T W, Wiley-Interscience, New York, 1981 whose disclosure is incorporated by reference herein. Suitable examples of hydroxyl protecting groups include silyl ethers, such as t-butyldimethyl or t-butyl-diphenyl, and alkyl ethers, such as methyl connected by an alkyl chain of variable link, $(CR_{10}R_{20})_n$.

Pharmaceutically acid addition salts of compounds of formula (I) may be obtained in known manner, for example by treatment thereof with an appropriate amount of acid in the presence of a suitable solvent.

The invention will now be described by reference to the following examples which are merely illustrative and are not to be construed as a limitation of the scope of the present invention.

SYNTHETIC EXAMPLES

Example 1

5-(3-Methoxyphenyl)-2-methyl-4-(4-pyridyl)oxazole (a) 2-Amino-1-(3-methoxyphenyl)-2-(4-pyridyl) acetophenone hydrochloride The title compound was prepared following the procedure of Murphy, J. G. *J. Org. Chem*, 1961, 26, 3104 except using 2-hydroxyimino-1-(3-methoxyphenyl)-2-(4-pyridyl) acetophenone [see PCT/US93/00674, Adams et al, published as WO93/14081].

(b) 2-Acetamido-1-(3-methoxyphenyl)-2-(4-pyridyl) ethanone

To a solution of 2-amino-3-methoxy-2-(4-pyridyl) acetophenone hydrochloride (0.5 g, 1.8 mmol) in pyridine (8 mL) was added acetic anhydride (1 mL). The mixture was stirred at rt for 45 min, then poured into $H_2O$. The layers were separated and the aqueous layer was extracted with $CH_2Cl_2$. The combined organic layers were washed with sat'd NaCl, then dried over $MgSO_4$. Evaporation of solvent gave a red oil which was purified by flash chromatography, eluting with a solvent gradient of 0–4% $MeOH/CHCl_3$. The title compound was isolated as a yellow oil (0.21 g).

(c) 5-(3-Methoxyphenyl)-2-methyl-4-(4-pyridyl)oxazole

The title compound was prepared using the procedure of Hayes, F. N. et al., *J. Amer. Chem Soc.*, 1955, 77, 1850 except using 2-acetamido-1-(3-methoxyphenyl)-2-(4-pyridyl)ethanone: ESMS (m/z): 267 ($M^+$+H).

Example 2

5-(4-Fluorophenyl)-2-methyl-4-(4-pyridyl)oxazole (a) 1-(4-Fluorophenyl)-2-(4-pyridyl)ethanone oxime To a solution of 4-fluorophenyl-2-(4-pyridyl) acetophenone (8.08 g, 37.6 mmol) [See PCT/US93/00674, Adams et al., WO93/14081] in EtOH (80 mL) was added hydroxylamine hydrochloride (4.12 g, 59.7 mmol) and pyridine (4.8 mL, 59.7 mmol). The mixture was stirred at 60 ° C. for 1 h, then poured into $H_2O$ and stirred an additional 1 min. The resulting precipitate was filtered and washed with $H_2O$. The precipitate was recrystallized from $EtOH/H_2O$ to give the title compound as a white solid (6.29 g): mp 135–136° C.

(b) 2-Acetamido-1-(4-fluorophenyl)-2-(4-pyridyl)ethanone

The title compound was prepared by the procedure of Shilcrat, S. C. et al., *J. Heterocyclic Chem*, 1991, 28, 1181 except using 1-(4-fluorophenyl)-2-(4-pyridyl)ethanone oxime and acetic anhydride.

(c) 5-(4-Fluorophenyl)-2-methyl-4-(4-pyridyl)oxazole

The title compound was prepared using the procedure of Hayes, F. N. et al, *J. Amer. Chem. Soc.*, 1955, 77, 1850 except using 2-acetamido-1-(4-fluorophenyl)-2-(4-pyridyl) ethanone: ESMS (m/z): 255 ($M^+$+H).

Example 3

2-Methyl-4-phenyl-5-(4-pyridyl)oxazole (a) 2-Phenyl-1-(4-pyridyl)acetophenone

A suspension of isonicotinoyl chloride (0.58 g, 3.26 mmol) in dry THF (7.0 mL) was cooled to −78° C., and benzyl magnesium chloride (3.4 mL, 6.85 mmol; 2.0 M soln in THF) was added dropwise. After the addition was complete, the ice bath was removed and the reaction mixture was allowed to warm to room temperature. After 3 h the reaction mixture was poured into saturated $NH_4Cl$ and the layers were separated. The aqueous mixture was extracted with THF. The combined organic layers were washed with sat'd NaCl and dried over $MgSO_4$. Evaporation of solvent gave a yellow solid which was purified by flash chromatography, eluting with a solvent gradient of 0–3% $MeOH/CH_2Cl_2$. The title compound was isolated as a yellow solid (0.50 g).

(b) 1-Hydroxyimino-1-phenyl-1-(4-pyridyl) ethanone

To a solution of 2-phenyl-1-(4-pyridyl)acetophenone (0.50 g, 2.53 mmol) in pyridine (7.5 mL) was added hydroxylamine hydrochloride (0.65 g, 9.36 mmol). After stirring at rt for 20 h, the pyridine was evaporated and the residue was taken up in $H_2O$ and filtered. The precipitate was washed with $H_2O$ and air-dried giving the title compound as a yellow solid (0.529 g).

(c) 2-Acetamido2-(4-phenyl)-1-(4-pyridyl)ethanone

Sodium (0.08 g, 3.50 mmol) was added to absolute EtOH (16 mL) and stirred. Upon completion of the reaction and cooling to ambient temperature, 1-Hydroxyimino-2-phenyl-1-(4-pyridyl)ethanone (0.53 g, 2.50 mmol) was added portionwise. After 15 min, the yellow reaction mixture was cooled in an ice-bath and p-toluenesulfonyl chloride (0.59 g, 3.07 mmol) was added in a single portion. The mixture was stirred at −5° C. for 2 h and then a solution of NaOEt [from sodium (0.07 g, 5.18 mmol) and absolute EtOH (3.3 mL)] was added dropwise. After 45 min, $Et_2O$ (9 mL) was added and the stirring was continued. After 30 min, the solvent was evaporated and the residue was partitioned between $Et_2O$ and 3N HCl. The layers were sepsrtated and the $Et_2O$ layer was extracted with HCl. The aqueous phase was evaporated to give a yellow oil (1.52 g) which was dissolved in pyridine (10 mL). Acetic anhydride (1 mL) was added and the reaction mixture was stirred at rt. After 19 h, the mixture was poured into $H_2O$ and $CH_2Cl_2$ was added. The layers were separated and the aqueous layer was extracted with $CH_2Cl_2$. The combined organic layers were washed with sat'd NaCl and dried over $MgSO_4$. Evaporation of solvent gave a red oil which was purified by flash chromatography, eluting with 0–3% $MeOH/CHCl_3$. The title compound was obtained as a gold oil (0.238 g).

(d) 2-Methyl-4-phenyl-5-(4-pyridyl)oxazole

A mixture of 2-acetamido-2-phenyl-1-(4-pyridyl) ethanone (0.101 g, 0.397 mmol) in conc. $H_2SO_4$ (1 mL) was heated at 100° C. for 18 h. After cooling, the mixture was poured onto ice and neutralized with 2.5N NaOH. The aqueous mixture was extracted with $CH_2Cl_2$ and the combined organic extracts were washed with sat'd NaCl and dried over $MgSO_4$. Evaporation of solvent gave an oil which was purified by flash chromatography, eluting with 0–2% $MeOH/CHCl_3$. The title compound was obtained as a gold oil (3.0 mg): MS(DCI/$NH_3$) (m/z): 237 ($M^+$+H).

Example 4

4-(4-Fluorophenyl)-2-methyl-5-(4-pyridyl)oxazole

To a solution of 4-fluorophenyl-2-(4-pyridyl) acetophenone [See PCT/US93/00674, Adams et al., published as WO93/14081](0.167 g, 0.76 mmol) in $CH_2Cl_2$ (5 mL) was added bromine (7.8 mL, 0.78 mmol; 0.1M soln in $CH_2Cl_2$). After stirring at room temperature for 30 min, the solvent was removed in vacuo and the solid was taken up in glacial acetic acid (10 mL). Sodium acetate (0.192 g, 2.34 mmol) and ammonium acetate (0.301 g, 3.9 mmol) were added and the reaction mixture was heated at reflux for 19 h. After cooling, the mixture was poured into $H_2O$, neutralized with conc. $NH_4OH$, then extracted exhaustively with $CH_2Cl_2$. The combined organic layers were washed with sat'd NaCl and dried over $MgSO_4$. Evaporation of solvent provided a yellow solid which was purified by flash chromatography, eluting with 100% $CHCl_3$. The title compound was obtained as a yellow waxy solid (0.067 g): ESMS (m/z): 255 ($M^+$+H).

Example 5

4-(4-Fluorophenyl)-2-phenyl-5-(4-pyridyl)oxazole (a) 2-Benzoyloxy-1-(4-fluorophenyl)-2-(4-pyridyl)ethanone To a solution of 4-fluorophenyl-2-(4-pyridyl) acetophenone [See PCT/US93/00674, Adams et al., published as WO93/14081 (0.356 g, 1.65 mmol) in $CH_2Cl_2$ (5 mL) was added bromine (18.1 mL, 1.81 mmol; 0.1M soln in $CH_2Cl_2$). After stirring at rt for 30 min, the solvent was removed in vacuo and the solid was taken up in EtOH (5 mL). Sodium benzoate (0.635 g, 4.4 mmol) and conc. $H_2SO_4$ (3 drops) were added and the mixture was heated at reflux for 18 h. After cooling, the mixture was poured into $H_2O$, neutralized with conc. $NH_4OH$, then extracted with EtOAc. The combined organic extracts were washed with sat'd NaCl and dried over $MgSO_4$. Evaporation of solvent gave a red oil which was filtered through a pad of silica gel, eluting with a solvent gradient of 100:0 to 50:1 $CHCl_3$/MeOH. The title compound was isolated as a yellow oil (0.131 g).

(b) 4-(4-Fluorophenyl)-2-phenyl-5-(4-pyridyl)oxazole

A solution of 2-benzoyloxy-1-(4-fluorophenyl)-2-(4-pyridyl)ethanone (0.131 g, 0.391 mmol) and ammonium acetate (0.28 g, 3.63 mmol) in glacial acetic acid (3 mL) was heated at reflux for 1.5 h. After cooling, the mixture was neutralized with conc. $NH_4OH$ and the solvent was removed in vacuo to give a yellow oil. Purification by flash chromatography (15–25% EtOAc/Hex) afforded the title compound as a white solid (9.0 mg): ESMS (m/z): 317 ($M^+$+H).

Example 6

2-Amino-4-(4-fluorophenyl)-5-(4-pyridyl)oxazole

A mixture of 1-(t-butyldimethylsilyloxy)-2-(4-fluorophenyl)-1-(4-pyridyl)ethanone [See Ex. 79 (a) of Adams et al., WO93/14081] (5.16 g, 15.0 mmol), cyanamide (0.95 g, 22.5 mmol) and KOH (0.55 g, 9.8 mmol) in EtOH (20 mL) was heated at reflux for 1 h. After cooling, the precipitate was filtered and washed with EtOH. Recrystallization from $CH_2Cl_2$/MeOH afforded the title compound as a yellow solid (0.38 g): ESMS (m/z): 256 ($M^+$+H).

Example 7

4-(4-Fluorophenyl)-5-(4-pyridyl)oxazole a) 4'-fluorophenyl-(tolylthio)methylformamide A soln of p-Fluorobenzaldehyde (13.1 mL, 122 mmol) thiocresol (16.64 g, 122 mmol), formamide (15.0 mL, 445 mmol), and toluene (300 mL) were combined and heated to toluene reflux with azeotropic removal of $H_2O$ for 18 h. The cooled reaction was diluted with EtOAc (500 mL) and washed with satd aq $Na_2CO_3$ (3×100 mL), satd aq NaCl (100 mL), dried ($Na_2SO_4$), and concentrated. The residue was triturated with petroleum ether, filtered and dried in vacuo to afford 28.50 g of the title compound as a white solid (85%). mp=119–120°.

b) 4'-fluorophenyl-(tolylthio)methylisocyanide

4'-Fluorophenyl-(tolylthio)methlylformamide (25 g, 91 mmol) in $CH_2Cl_2$ (300 mL) was cooled to −30 ° and, with mechanical stirring, $POCl_3$ (11 mL, 110 mmol) was added dropwise followed by the dropwise addition of $Et_3N$ (45 mL, 320 mmol) with the temperature maintained below −30°. Stirred at −30° for 30 min and 5° for 2 h, diluted with $CH_2Cl_2$ (300 mL) and washed with 5% aq $Na_2CO_3$ (3×100 mL), dried ($Na_2SO_4$) and concentrated to 500 mL. This soln was filtered through a 12×16 cm cylinder of silica in a large sintered glass funnel with $CH_2Cl_2$ to afford 12.5 g (53%) of purified isonitrile as a light brown, waxy solid. IR ($CH_2Cl_2$) 2130 $cm^{-1}$.

c) 4-(4-Fluorophenyl)-5-(4-pyridyl)oxazole

4-Flourophenyl-(tolylthio)methylisocyanide (2.57 g, 10 mmol), pyridine-4-carboxaldehyde (1.07 g, 10 mmol) and $CH_2Cl_2$ (20 mL) were stirred under Ar at −15° (ice-methanol bath) and TBD (1.39 g, 10 mmol) was added portionwise. The reaction temperature rose to 5° before recooling to −15°. The reaction was allowed to warm to 4° and was kept at that temperature for 18 h, diluted with EtOAc (100 mL) and washed with 10% aq $Na_2CO_3$ (3×25 ml). The EtOAc was then extracted with 1 N HCl (3×15 mL) and crystals formed from the aqueous phase. After standing for 1 h at 23° the crystals were filtered off, washed with abs EtOH (25 ml) and $Et_2O$ (2×25 mL) and dried in vacuo to afford 1.47 g (53%) of the title cmpd as the hydrochloride. The aq filtrate was washed with EtOAC (2×40 mL) and made basic by the careful addition of solid $K_2CO_3$. Extraction of with EtOAc (3×40 ml) drying ($Na_2SO_4$) concentration and crystallization of the residue (hexane/acetone) afforded an additional 0.426 g (18%) of the title compound as the free base, mp (free base)=110–111°.

Example 8

4-(4-Fluorophenyl)-5-(2-methylpyrid-4-yl)oxazole

The compound of example 7(b) (0.599 g, 2.33 mmol) and 2-methylpyridine 4-carboxaldehyde (257 mg, 2.12 mmol) and $CH_2Cl_2$ (4 ml) were reacted by the procedure of Example 7. The resulting reaction was worked up by dilution with EtOAc (40 mL), washing with satd aq $Na_2CO_3$ (2×15 mL), extraction of the EtOAc with 1N HCl (3×15 mL). The combined aq phases were washed with EtOAc (3×25 mL) and then made basic by the careful addition of $K_2CO_3$. Extraction of the aq with EtOAc (4×40 mL), drying ($Na_2SO_4$) and concentration afforded a tan oil which could not be made to solidify. The residue was dissolved in 9:1 $Et_2O$/acetone (20 mL) and 1 N etherial HCl (3 mL) was added. The precipitated solid was washed with $Et_2O$ and dried in vacuo to afford 471 mg (79%) of the title compound as the hydrochloride, mp=198–200 (dec).

Example 9

4-(3,4-Dichlorophenyl)-5-(4-pyridyl)oxazole

Using the method of example 7 (a,b,c) substituting 3,4,-dichlorobenzaldehyde for 4-fluorobenzalderyde the title compound was prepared. mp=142°.

Example 10

4-(3-Chlorophenyl)-5-(4-pyridyl)oxazole

Using the method of example 7 (a,b,c) substituting 3-chlorobenzaldehyde for 4-fluorobenzaldehyde the titile compound was prepared. mp=125–126°.

Example 11

4-(4-Fluorophenyl)-2-(4-methylthiophenyl)-5-(4-pyridyl)oxazole (a) 2-(4-Fluorophenyl)-1-(4-pyridyl)-2-oxoethyl 4-methylthiobezoate and 1-(4-Fluorophenyl)-2-(4-pyridyl)-2-oxoethyl 4-methylthiobenzoate The title compounds were prepared using the same procedure of Lantos et al. (*J. Med. Chem.* 1984, 27, 72) whose disclosure is incorporated by reference herein, and used to prepare 1-(4-fluorophenyl)-2-(4-pyridyl)-2-oxoethyl benzoate and 2-(4-fluorophenyl)-1-(4-pyridyl)-2-oxoethyl benzoate, except using 1-cyano-1-(4-pyridyl)methyl 4-methylthiobenzoate.

(b) 4-(4-Fluorophenyl)-2-(4-methylthiophenyl)-5-(4-pyridyl)oxazole

To a solution containing a mixture of 2-(4-fluorophenyl)-1-(4-pyridyl)-2-oxoethyl 4-methylthiobenzoate and 1-(4-fluorophenyl)-2-(4-pyridyl)-2-oxoethyl 4 methylthiobenzoate (1.0 g, 2.62 mmol) in glacial acetic acid (50 mL) was added ammonium acetate (2.0 g, 26.2 mmol). The resulting mixture was heated at reflux for 1.5 h, then allowed to cool. The mixture was poured into $H_2O$, neutralized with conc. $NH_4OH$ and extracted with $CH_2Cl_2$. The combined organic extracts were washed with sat'd NaCl and dried over $MgSO_4$. Purification by column chromatography, eluting with 5:1 to 1:1 Hex/EtOAc afforded the title compound (77.6 mg) as a yellow solid: ESMS (m/z): 363.0 ($M^+$+H).

Example 12

4-(4-Fluorophenyl)-2-[4-(methylsulfinyl)phenyl]-5-(4-pyridyl)oxazole

To a mixture of 4-(4-fluorophenyl)-2-(4methylthiophenyl)-5-(4-pyridyl)oxazole (0.056 g, 0.15 mmol) in glacial acetic acid (12 mL) was added a solution of $K_2S_2O_8$ (0.07 g, 024 mmol) in $H_2O$ (2 mL). After stirring at rt for 48 hr, the precipitate was filtered. Purification by column chromatography (25:1 $CH_2Cl_2$/MeOH), followed by trituration with $Et_2O$ afforded the title compound (0.014 g) as a white solid: ESMS (m/z)=379.0 ($M^+$+H).

Example 13

2-Acetamido-4-(4-fluorophenyl)-5-(4-pyridyl) oxazole

A mixture of 2-amino-4-(4-fluorophenyl)-5-(4-pyridyl) oxazole (0.090 g, 0.353 mmol) in acetic anhydride (4 mL) was stirred at room temperature. After 72 h the mixture was poured into $H_2O$ and neutralized with conc. $NH_4OH$. The resulting precipitate was filtered and washed with $H_2O$. Purification by column chromatography (0–5% MeOH/ $CHCl_3$), followed by recrystallization from MeOH afforded the title compound as a white solid (30.0 mg):ESMS (m/z): 298.0 ($M^+$+H).

Example 14

4-(4-Fluorophenyl)-5-(2-amino4-pyrimidinyl) oxazole a) 1-N,N-dimethylamino-(4,4-dimethoxy)buten-3-one Pyruvic aldehyde dimethyl acetal (50 ml, 0.4106 mol) and N,N-Dimethylformamide dimethyl acetal (54.5 ml,0.4106 mol) were mixed neat and heated to 80 ° C. for eighteen hours. Crude product (95.0 g) was used without further purification.

b) 2Amino-4(dimethoxymethyl)pyrimidine

Guanidine HCl (43 g) was mixed in water (150 ml) and added to 1-N,N-dimethylamino-(4,4-dimethoxy)buten-3-one (95.0 g,crude) at room temperature. Sodium hyroxide was mixed in water and added to reaction mixture at room temperature. The reaction was then heated to 60° C. for eighteeen hours. A percipitate formed and was filtered and washed with water. The crude product (32.5 g) was used without further purification.

c) 2-Amino-(pyrimidinyl)aldehyde

2-Amino-4-(dimethoxymethyl)pyrimidine( 6.6g, 0.0390 mol) was mixed in 3N HCl (29.96 ml, 0.0858) neat and heated to 47° C. for sixteen hours. The reaction was cooled to room temperature and ethyl acetate (150 ml) was added. $NaHCO_3$ (16.17 g, 0.1716 mol) was then added slowly. The mixture was stirred and the organic layer decanted, this was repeated a total of five times. The organic phases were combined and evaporated to yield the product—a yellow solid (2.33g, 48%). $^1H$ NMR (400 MHz,$CDCl_3$) δ9.80 (s, 1H), 8.50 (d, 1H), 7.08 (d, 1H) 5.25 (s broad, 2H).

d) 2-Aminopyrimidine-[2,2,6,6-tetramethylpiperidinyl] imine

2-Amino-(pyrimidin-4-yl)aldehyde (2.33 g, 0.0189 mol) and 4-Amino-(2,2,6,6-tetramethyl)piperidine (3.24 ml, 0.0189) were mixed in $CH_2Cl_2$ at room temperature for eight hours to yield the crude product (which contains the imine plus a large, approx. equal amount of unreacted 2-amino-(pyrimidin-4-yl)aldehyde) (4.92 g) which was used without further purification. $^1H$ NMR (400 MHz, $CDCl_3$) δ8.38 (d, 1H), 8.20 (s, 1H), 7.25 (d, 1H), 5.10 (s broad, 2H), 1.79 (m, 1H) 1.70 ( m, 1H), 1.40(t, 2H), 1.30–1.00 (m, 12H),0.85 ( t, 2H).

e) 4-(4-Fluorophenyl)-5-(2-amino-4-pyrimidinyl)oxazole

The crude mixture from step (d) above (4.92 g) was mixed in $CH_2Cl_2$ and cooled to 0° C. 4'-Fluorophenyl(tolylthio) methylisocyanide (4.86 g, 0.0189 mol—refer to Example 7 a) and 7 b) above) and 1.5.7.triazabicyclo[4.4.0.]dec-5-ene (2.63 g, 0.0189 mol) were mixed in $CH_2Cl_2$ and added dropwise to the cold reaction mixture. The reaction was kept cold for forty-eight hours. The solvent was evaporated and the crude mixture purified by flash chromatography (silica gel, $CH_2Cl_2$/methanol) to yield two products; an imidazole derivative [4-(4-Fluorophenyl)-5-(2-amino-4-pyrimidinyl)- pyrazole] and the title compound (550 mg). $^1H$ NMR δ8.36 ( d,1H), 8.05 (s,1H), 7.95 (m, 2H), 7.15 (m, 2H), 6.95 (d, 1H), 5.10 (s broad, 2H),

Methods of Treatment

The compounds of Formula (I) or a pharmaceutically acceptable salt thereof can be used in the manufacture of a medicament for the prophylactic or therapeutic treatment of any disease state in a human, or other mammal, which is excacerbated or caused by excessive or unregulated cytokine production by such mammal's cell, such as, but not limited to monocytes and/or macrophages.

Compounds of formula (I) are capable of inhibiting proinflammatory cytokines, such as IL-1, IL6, IL8 and TNF and are therefore of use in therapy. IL-1, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides a method of treating a cytokine-mediated disease which comprises administering an effective cytokine-interfering amount of a compound of formula (I) or a pharmaceutically acceptable salt thereof.

In a specific embodiment the present invention provides for a method of treating inflammation in a mammal which method comprises administering an effective amount of a compound of formula (I) or a pharmaceutically acceptable salt thereof. Another specific embodiment of the present invention provides for a method of treating stroke, asthma, ARDS, ischemia, and/or arthritis in a mammal which method comprises administering an effective amount of a compound of formula (I) or a pharmaceutically acceptable salt thereof.

In particular, compounds of formula (I) or a pharmaceutically acceptable salt thereof are of use in the prophylaxis or therapy of any disease state in a human, or other mammal, which is exacerbated by or caused by excessive or unregulated IL-1, IL-8 or TNF production by such mammal's cell, such as, but not limited to, monocytes and/or macrophages.

Accordingly, in another aspect, this invention relates to a method of inhibiting the production of IL-1 in a mammal in need thereof which comprises administering to said mammal an effective amount of a compound of formula (I) or a pharmaceutically acceptable salt thereof.

There are many disease states in which excessive or unregulated IL-1 production is implicated in exacerbating and/or causing the disease. These include arthritis, rheumatoid arthritis, osteoarthritis, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, rheumatoid arthritis, gout, traumatic arthritis, rubella arthritis and acute synovitis. Recent evidence also links IL-1 activity to diabetes, pancreatic β cells and Alzheimer's disease.

In a further aspect, this invention relates to a method of inhibiting the production of TNF in a mammal in need thereof which comprises administering to said mammal an effective amount of a compound of formula (I) or a pharmaceutically acceptable salt thereof.

Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, such as osteoporosis, reperfusion injury, stroke, graft vs. host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis and pyresis.

Compounds of formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of formula (I). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal, preferably a human, afflicted with a human immunodeficiency virus (HIV) which comprises administering to such mammal an effective TNF inhibiting amount of a compound of formula (I) or a pharmaceutically acceptable salt thereof.

Compounds of formula (I) may also be used in association with the veterinary treatment of mammals, other than in humans, in need of inhibition of TNF production.

TNF mediated diseases for treatment, therapeutically or prophylactically, in animals include disease states such as those noted above, but in particular viral infections. Examples of such viruses include, but are not limited to, the lentivirus infections such as equine infectious anaemia virus, caprine arthritis virus, visna virus, or the maedi virus, or the retroviruses, such as feline immunodeficiency virus (FIV), bovine immunodeficiency virus, or canine immunodeficiency virus.

The compounds of formula (I) may also be used topically in the treatment or prophylaxis of topical disease states mediated by or exacerbated by excessive cytokine production, such as by IL-1 or TNF respectively, such as inflamed joints, eczema, psoriasis and other inflammatory skin conditions such as sunburn; inflammatory eye conditions including conjunctivitis; pyresis, pain and other conditions associated with inflammation.

Compounds of formula (I) have also been shown to inhibit the production of IL-8 (Interleukin-8, NAP). Accordingly, in a further aspect, this invention relates to a method of inhibiting the production of IL-8 in a mammal in need thereof which comprises administering to said mammal an effective amount of a compound of formula (I) or a pharmaceutically acceptable salt thereof.

There are many disease states m which excessive or unregulated IL-8 production is implicated in exacerbating and/or causing the disease. These diseases are characterized by massive neutrophil infiltration such as, psoriasis, inflammatory bowel disease, asthma, cardiac and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to-a direct reduction in the neutrophil infiltration.

The compounds of formula (I) are administered in an amount sufficient to inhibit cytokine, in particular IL-1, IL-8 or TNF, production such that it is regulated down to normal levels, or in some case to subnormal levels, so as to ameliorate or prevent the disease state. Abnormal levels of IL-1, IL-8 or TNF, for instance in the context of the present invention, constitute: (i) levels of free (not cell bound) IL-1, IL-8 or TNF greater than or equal to 1 picogram per ml; (ii) any cell associated IL-1, IL-8 or TNF; or (iii) the presence of IL-1, IL-8 or TNF mRNA above basal levels in cells or tissues in which IL-1, IL-8 or TNF, respectively, is produced.

The discovery that the compounds of formula (I) are inhibitors of cytokines, specifically IL-1, IL-8 and TNF is based upon the effects of the compounds of formulas (I) on the production of the IL-1, IL-8 and TNF in in vitro assays which are described herein.

As used herein, the term "inhibiting the production of IL-1 (IL-8 or TNF)" refers to:
  a) a decrease of excessive in vivo levels of the cytokine (IL-1, IL-8 or TNF) in a human to normal or subnormal levels by inhibition of the in vivo release of the cytokine by all cells, including but not limited to monocytes or macrophages;
  b) a down regulation, at the genomic level, of excessive in vivo levels of the cytokine (IL-1, IL-8 or TFN) in a human to normal or sub-normal levels;
  c) a down regulation, by inhibition of the direct synthesis of the cytokine (IL-1, IL-8 or TNF) as a postranslational event; or
  d) a down regulation, at the translational level, of excessive in vivo levels of the cytokine (IL-1, IL8 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease stated mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphoctye cells. Examples of cytokines include, but are not limited to, Interleukin-1 (IL-1), Interleukin-6 (IL6), Interleukin-8 (IL8), Tumor Necrosis Factor-alpha (TNF-$\alpha$) and Tumor Necrosis Factor. beta (TNF-$\beta$).

As used herein, the term "cytokine interfering" or "cytokine suppressive amount" refers to an effective amount of a compound of formula (I) which will cause a decrease in the in vivo levels of the cytokine to normal or subnormal levels, when given to a patient for the prophylaxis or treatment of a disease state which is exacerbated by, or caused by, excessive or unregulated cytokine production.

As used herein, the cytokine referred to in the phrase "inhibition of a cytokine, for use in the treatment of a HIV-infected human" is a cytokine which is implicated in (a) the initiation and/or maintenance of T cell activation and/or activated T cell-mediated HIV gene expression and/or replication and/or (b) any cytokine-mediated disease associated problem such as cachexia or muscle degeneration.

As TNF-β (also known as lymphotoxin) has close structural homology with TNF-α (also known as cachectin) and since each induces similar biologic responses and binds to the same cellular receptor, both TNF-α and TNF-β are inhibited by the compounds of the present invention and thus are herein referred to collectively as "TNF" unless specifically delineated otherwise.

In order to use a compound of formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of formula (I) and a pharmaceutically acceptable carrier or diluent.

Compounds of formula (I), pharmaceutically acceptable salts thereof and pharmaceutical compositions incorporating such may conveniently be administered by any of the routes conventionally used for drug administration, for instance, orally, topically, parenterally or by inhalation. The compounds of formula (I) may be administered in conventional dosage forms prepared by combining a compound of formula (I) with standard pharmaceutical carriers according to conventional procedures. The compounds of formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of formula (I) may be administered topically, that is by non-systemic administration. This includes the application of a compound of formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan esteror a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of formula (I), the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, ie., the number of doses of a compound of formula (I) or a pharmaceutically acceptable salt thereof given per day for a defined number of days, can be ascertained by those skilled in the art using conventional course of treatment determination tests.

The invention will now be described by reference to the following examples which are merely illustrative and are not to be construed as a limitation of the scope of the present invention.

Biological Examples

The cytokine-inhibiting effects of compounds of the present invention are determined by the following in vitro assays:

Interleukin 1 (IL-1)

Human peripheral blood monocytes were isolated and purified from either fresh blood preparations from volunteer donors, or from blood bank buffy coats, according to the procedure of Colotta et al, J Immunol, 132,936 (1984). These monocytes ($1 \times 10^6$) were plated in 24-well plates at a concentration of 1–2 million/ml per well. The cells were allowed to adhere for 2 hours, after which time non-adherent cells were removed by gentle washing. Test compounds were then added to the cells for 1h before the addition of lipopolysaccharide (50 ng/ml), and the cultures were incubated at 37° C. for an additional 24h. At the end of this period, culture supernatants were removed and clarified of cells and all debris. Culture supernatants were then immediately assayed for IL-1 biological activity, either by the method of Simon et al., J. Immunol. Methods, 84, 85, (1985) (based on ability of IL-1 to stimulate a Interleukin 2 producing cell line (EL-4) to secrete IL-2, in concert with A23187 ionophore) or the method of Lee et al., J. ImmunoTherapy, 6 (1), 1–12 (1990) (ELISA assay). Compounds of formula (I) as illustrated by Examples 1, 2, and 7 herein were shown to be inhibitors of in vitro IL-1 produced by human monocytes.

Tumor Necrosis Factor (TNF)

Human peripheral blood monocytes are isolated and purified from either blood bank buffy coats or plateletpheresis residues, according to the procedure of Colotta, R. et al., J Immunol, 132(2), 936 (1984). The monocytes are plated at a density of $1 \times 10^6$ cells/ml medium/well in 24-well multidishes. The cells are allowed to adhere for 1 hour after which time the supernatant is aspirated and fresh medium (1 ml, RPMI-1640, Whitaker Biomedical Products, Whitaker, Calif.) containing 1% fetal calf serum plus penicillin and streptomycin (10 units/ml) added. The cells are incubated for 45 minutes in the presence or absence of a test compound at 1 nM–10 mM dose ranges (compounds were solubilized in dimethyl sulfoxide/ethanol, such that the final solvent concentration in the culture medium is 0.5% dimethyl sulfoxide/0.5% ethanol). Bacterial lipopoly-saccharide (*E. coli* 055:B5 [LPS] from Sigma Chemicals Co.) is then added (100 ng/ml in 10 ml phosphate buffered saline) and cultures incubated for 16–18 hours at 37° C. in a 5% $CO_2$ incubator. At the end of the incubation period, culture supernatants are removed from the cells, centrifuged at 3000 rpm to remove cell debris. The supernatant is then assayed for TNF activity using either a radio-immuno or an ELISA assay, as described in WO 92/10190 and by Becker et al., J Immunol, 1991, 147,4307.

Interleukin 8 (IL8)

Primary human umbilical cord endothelial cells (HUVEC) (Cell Systems, Kirland, Wash.) are maintained in culture medium supplemented with 15% fetal bovine serum and 1% CS-HBGF consisting of aFGF and heparin. The cells are then diluted 20-fold before being plated (250 μl) into gelating coated 96-well plates. Prior to use, culture medium is replaced with fresh medium (200 μl). Buffer or test compound (25 μl; at concentrations between 1 and 10 μM) is then added to each well in quadruplicate wells and the plates incubated for 6h in a humidified incubator at 37° C. in an atmosphere of 5% $CO_2$. At the end of the incubation period, supernatant is removed and assayed for IL-8 concentration using an IL-8 ELISA kit obtained from R&D Systems (Minneapolis, Minn.). All data is presented as mean value (ng/ml) of multiple samples based on the standard curve. $IC_{50}$.s where appropriate are generated by non-linear regression analysis.

Cytokine Specific Binding Protein Assay

A radiocompetitive binding assay was developed to provide a highly reproducible primary screen for structure-activity studies. This assay provides many advantages over the conventional bioassays which utilize freshly isolated human monocytes as a source of cytokines and ELISA assays to quantify them. Besides being a much more facile assay, the binding assay has been extensively validated to highly correlate with the results of the bioassay. A specific and reproducible binding assay was developed to test compounds belonging to the CSAID™ class of compounds using soluble cystosolic fraction from THP.1 cells and a radiolabeled compound. For instance, a suitable radiolabeled compound of the CSAID™ class of compounds is 4-(Fluorophenyl)-2-(4-hydroxyphenyl-3,5-$t_2$)-5-(4-pyridyl) imidazole which may be made in an analagous procedures as demonstrated in Adams et al., WO93/14081 or as illustrated below.

In brief, the THP.1 cytosol was routinely prepared from cell lysate obtained by nitrogen cavitation followed by a 10 K×g low speed and a 100 K×g high speed centrifugation, the supernatant of which was designated as the cytosolic fraction. THP.1 cytosol was incubated with appropriately diluted radioligand at room temperature for a pre-determined time to allow the binding to achieve equilibrium. The sample was added to a G-10 column and eluted with 20 mm TRN, 50 mMb-mercaptoethanol, $NaN_3$. The fraction encompassing the void volume was collected and the radioactivity was assessed by liquid scintillation counting. This was determined to reflect bound radioligand since the radioactive signal was abrogated by the presence of excess cold ligand in the incubation mixture or when there was no cytosolic fraction present. Compounds of Formula (I) at various doses were added to the binding assay to achieve inhibition of binding of the radiolabel. $IC_{50}$s as well as Ki values were determined by regression analysis and scatchard plot analysis respectively. There is generally excellent correlation between the $IC_{50}$ of compounds tested in both the binding assay and the bioassay and can be used interchangeably in many cases. Compounds of Formula (I) as illustrated by Examples 1 to 14 herein were shown to have activity in the CSBP assay.

Patent Application U.S. Ser. No. 08/123,175 Lee et al., filed September 1993, whose disclosure is incorporated by reference herein in its entirety also describes the above noted method for screening drugs to identify compounds which interact with and bind to the CSBP. However, for purposes herein, the binding protein may be in isolated form in solution, or in immobilized form, or may be genetically engineered to be expressed on the surface of recombinant host cells such as in phage display system or as fusion proteins. Alternatively, whole cells or cytosolic fractions comprising the CSBP may be employed in the creening protocol. Regardless of the form of the binding protein, a plurality of compounds are contacted with the binding protein under conditions sufficient to form a compound/ binding protein complex and compound capable of forming, enhancing or interfering with said complexes are detected.

More specifically, the Cytokine Specific Binding Assay is performed as follows:

MATERIALS

Incubation buffer: 20 mM Tris, 1 mM $MgCl_2$, 20 mM Hepes, 0.02% $NaN_3$, store at 4° C. Elution buffer: 20 mM Tris, 50 mM 2-mercaptoethanol, $NaN_3$, store at 4° C.

G-10 Sephadex: add 100 g Sephadex G-10 (Pharmacia, Uppsala, Sweden) to 400 mL dd $H_2O$ and allow to swell at room temperature for 2 hours. Decant fines and wash 3 times. Add $NaN_3$ and qs with dd $H_2O$ to 500 mLs and store at 4° C.

Assemble Columns: Straw column, filter frit and tip (Kontes, SP 420160-000, 420162-002). Lowsorb tubes (Nunc) used in binding reaction. THP.1 cytosol spun at 15000 rpm for 5 min to clarify. THP.1 cytosol prepared by hypnotic treatment of cells and lysis by decompression in nitrogen. Nuclei and membrane fragments removed by differential centrifugation (10,000 g for 1 hour and 100,000 g for 1 hour).

Compounds: Non-radioactive Compound I with corresponding EtOH control (dilutions made in incubation buffer) and $^3$H-Compound I (dilutions in incubation buffer).

METHOD

A. Column Preparation

1) Begin 30 min before anticipated elution of reaction mixture; 2) Add 3 mL of G-10 slurry to column for bed vol of 1.5 ml; 3) Rinse with 7 mL elution buffer (fill to top of column); 4) Cut columns down to size.

B. Sample Incubation 1) 15 min incubation at 4° C.; 2) Binding reaction mixture; 100 μL cytosol, 10 μL cold Compound I or EtOH control, 10 μL $^3$H-Compound I (molar concentration depends on nature of study); 3) "Free" control=100 μL incubation buffer in lieu of cytosol preparation.

C. Sample Elution

1) Elute at 4° C.; 2) Add total reaction volume to G-10 column; 3) Add 400 μL elution buffer to column and discard eluate; 4) Add 500 μL elution buffer to column, collecting eluted volume in 20 ml scintillation vial; 5) Add 15 mL Ready Safe scintillation fluid; 6) Vortex and count in liquid scintillation counter for 5 minutes. Include a "total input counts control" (10 μL of labeled ligand).

D. Data Analysis

1) Plot DPMS as output in graphic form and analyze by regression analysis and "Lundon ligand binding" software for the determination of IC 50 and Kd/Ki respectively; 2) Rank order the IC50s of the tested compounds in the CSAIDbioassay and compare to that generated by the CSAID binding assay and establish a correlation curve.

The binding assay was further validated by the following criteria, i.e. THP.1 cytosol demonstrated saturable and specific binding of the radiolabeled compound.

Preparation of 4-(Fluorophenyl)-2-(4-hydroxyphenyl-3,5-$t_2$)-5-(4-pyridyl)imidazole, (Compound I)

A 2.9 mg (0.0059 mmol) portion of 2-(3,5-Dibromo-4-hydroxyphenyl)-4-(4-fluorophenyl)-5-(4-pyridyl)imidazole, Compound I, was dissolved in 0.95 mL of dry DMF and 0.05 mL of triethylamine in a 2.4 mL round bottom flask equipped with a small magnetic stirring bar. A 1.7 mg portion of 5% Pd/C (Engelhard lot 28845) was added, and the flask was attached to the stainless steel tritium manifold. The mixture was degassed through four freeze-pump-thaw cycles, then tritium gas (5.3 Ci, 0.091 mmol) was introduced. The reaction mixture was allowed to warm to room temperature and was stirred vigorously for 20h. The mixture was frozen in liquid nitrogen, the remaining tritium gas (2.4 Ci) was removed, and the flask was removed from the manifold. The reaction mixture was transferred, using 3×1 mL of methanol as rinsings, into a 10 mL round bottom flask, and the solvents were removed by static vacuum transfer. A 1.5 mL portion of methanol was added to the residue, then removed by static vacuum transfer. The latter process was repeated. Finally, the residue was suspended in 1.5 mL of ethanol and filtered through a syringe-tip Millipore filter (0.45 micron), along with 3×ca. 1 mL ethanol rinsings. The total filtrate volume was determined to be 3.9 mL, and the total radioactivity, 94.2 mCi. Solution was determined to be 3.9 mL, and the total radioactivity, 94.2 mCi. HPLC analysis of filtrate (Partisil 5 ODS-3, 4.6 mm I.D.×25 cm, 1 mL/min of 70:30:01 water/acetonitrile/trifluoroacetic acid, Radiomatic Flo-One Beta radio detector with 3 mL/min of Ecoscint-H cocktail through a 0.75 mL cell) showed the presence of Compound I ($R_t$=60 min. ca. 37% of total radioactivity), and a discrete intermediate presumed to be the monobromo derivative Compound Ia ($R_t$=11.8 min, ca. 9%).

The filtrate solution was evaporated to near dryness with a stream of nitrogen, and the residue was dissolved in about 1.2 mL of the HPLC mobile phase. The solution was separated by HPLC as shown below, and the peaks corresponding to Compounds I and Ia and SB collected separately.

| HPLC Method | |
|---|---|
| Column | Altex Ultrasphere |
| | 10 mm I.D. × 25 cm |
| Mobile Phase | 70:30:0.1 |
| | water/acetonitrile/trifluoroacetic acid |
| Flow Rate | 5 mL/min |
| UV detection | 210 nm |
| Injection Volumes | 0.05–0.4 m: |
| Retention Times | 7.8 min Compound I |
| | 24 min Compound Ia |

The pooled Compound I fractions totaled 32 mL in volume and the radioactive concentration was 1.52 mCi/mL (total 48.6 m Ci). The pooled SB Compound Ia [$^3$H] fractions (totaling 10.1 mCi) were evaporated to dryness and the residue was transferred quantitatively into a glass vial using 3.8 mL of absolute ethanol for further analysis.

An 8 mL (12.2 mCi) portion of Compound I was evaporated to dryness in vacuo at <35° C., then redissolved in 0.5 mL of mobile phase. The whole volume was injected into the HPLC system described above, and the appropriate peak was collected. Evaporation of the collected eluate in vacuo at <35° C. and transfer of the yellow residue into a vial with absolute ethanol provided a solution (3.8 mL, 2.44 mCi/mL) of Compound I. The portion of this solution used for NMR analyses was first evaporated to dryness using stream of nitrogen then taken up in $CD_3OD$.

Analysis of 4-(4-Fluorophenyl)-2-(4-hydroxyphenyl-3,5-$t_2$)-5-(4-pyridyl)imidazole, Compound I.

| Radiochemical Purity by HPLC | |
|---|---|
| Method | |
| Column | Ultrasphere Octyl, 5 mm, 4.6 mm |
| | I.D. × 25 cm, Beckman |

-continued

| | |
|---|---|
| Mobile Phase | 350:150:0.5 (v/v/v) water/acetonitrile/trifluoroacetic acid |
| Flow Rate | 1.0 mL/min |
| Mass detection | UV at 210 nm |
| Radioactivity detection | Ramona-D radioactivity flow detector |
| Scintillator | Tru-Count Tru-Lab Supply Co.) |
| Flow rate | 5.0 mL/min |
| Cell volume | 0.75 mL |
| Retention time | 7.7 min |
| Result | 98.7 |

Radioactive Concentration by Scintillation Counting

| | |
|---|---|
| Method | |
| Scintillator | Ready Safe (Beckman Instruments, Inc.) |
| Instrument | TM Analytic model 6881 |
| Efficiency | Automated DPM calculation from quench curve |
| Result | 2.44 mCi/mL |

Specific Activity by Mass Spectrometry

| | |
|---|---|
| Method | CI-MS, $NH_3$ reagent gas |
| Result | 20.0 Ci/mmol |
| | $^3$H Distribution: |
| | Unlabeled 44% |
| | Single Label 43% |
| | Double Label 13% |

$^3$H NMR$^9$

| | |
|---|---|
| Method | |
| Instrument | Brunker AM 400 |
| Experiment | Proton decoupled $^3$H NMR |
| | Proton non-decoupled $^3$H NMR |
| | Proton non-decoupled $^3$H NMR |
| Peak Referencing Solvent | Solvent Peak: of methanol ∂ 3.3 |
| Solvent | Methanol-$d_4$ |
| Result | Tritium is incorporated exclusively on the carbon atoms ortho to aromatic hydroxyl group |

Analytical Summary

| Assay | Result |
|---|---|
| Radiochemical purity determined by HPLC | 98.7% |
| Radioactivity concentration determined by scintillation counting | 2.44 mCi/mL |
| Specific activity determined by mass spectrometry | 20.0 Ci/mmol |
| $^3$H NMR | agrees with the proposed structure |

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of the formula:

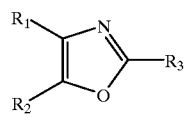

(I)

wherein:
one of $R_1$ or $R_2$ is an optionally substituted aryl ring and the other of $R_1$ or $R_2$ is an optionally substituted 4-pyridyl ring;
wherein when one of $R_1$ and $R_2$ is an optionally substituted aryl ring, the ring is substituted by one or two substituents, each of which is independently selected from a group consisting of a 4-phenyl, 4-naphth-1-yl or 5-naphth-2-yl substituent, is halo, cyano, $C(Z)NR_7R_{17}$, $C(Z)OR_{23}$, $(CR_{10}R_{20})_mCOR_{36}$, $SR_5$, $SOR_5$, $OR_{36}$, halo-substituted-$C_{1-4}$ alkyl, $C_{1-4}$ alkyl, $ZC(Z)R_{36}$, $NR_{10}C(Z)R_{23}$, and $(CR_{10}R_{20})_m NR_{10}R_{20}$;
and other positions of substitution, is halo, $(CR_{10}R_{20})_{m''}$--cyano, $C(Z)NR_{16}R_{26}$, $C(Z)OR_8$, $(CR_{10}R_{20})_{m''}COR_8$, $(CR_{10}R_{20})_{m''}S(O)_mR_8$, $(CR_{10}R_{20})_{m''}OR_8$, halo-substituted-$C_{1-4}$ alkyl, $C_{1-4}$ alkyl, $(CR_{10}R_{20})_{m''}NR_{10}C(Z)R_8$, $(CR_{10}R_{20})_{m''}NR_{10}S(O)_{m'}R_{11}$, $(CR_{10}R_{20})_{m''}NR_{10}S(O)_{m'}-NR_7R_{17}$, $(CR_{10}R_{20})_{m''}ZC(Z)R_8$ and $(CR_{10}R_{20})_{m''}NR_{16}R_{26}$;
and when one of $R_1$ and $R_2$ is the optionally substituted 4-pyridyl ring, the said ring is substituted by one or two substituents each of which is independently selected from $C_{1-4}$ alkyl, halo, $C_{1-4}$ alkoxy, $C_{1-4}$ alkylthio, $NR_{10}R_{20}$, or an N-heterocyclyl ring which ring has from 5 to 7 members and optionally contains an additional heteroatom selected from oxygen, sulfur and $NR_{22}$;
$R_3$ is hydrogen, $(CR_{10}R_{20})_n(Y_2)_p$, or halosubstituted $C_{1-10}$ alkyl;
t is an integer having a value of 1 to 3;
p is 0 or an integer having a value of 1, provided that when p is 0 then $Y_2$ is hydrogen;
Z is oxygen or sulfur;
n is 0 or an integer having a value of 1 to 10;
n' is an integer having a value of 1 to 10;
m is 0, or the integer 1 or 2;
m' is 1 or 2;
m" is 0 or an integer having a value of 1 to 5;
$Y_2$ is halogen, $OR_8$, $NO_2$, $S(O)_{m'}R_{11}$, $SR_8$, $S(O)_{m'}NR_8R_9$, $NR_8R_9$, $O(CR_{10}R_{20})_{n'}NR_8R_9$, $C(O)R_8$, $CO_2R_8$, $CO_2(CR_{10}R_{20})_{n'}CONR_8R_9$, $ZC(O)R_8$, $CN$, $C(Z)NR_8R_9$, $NR_{10}C(Z)R_8$, $C(Z)NR_8OR_9$, $NR_{10}C(Z)NR_8R_9$, $NR_{10}S(O)_{m'}R_{11}$, $N(OR_{21})C(Z)NR_8R_9$, $N(OR_{21})C(Z)R_8$, $C(=NOR_{21})R_8$, $NR_{10}C(=NR_{15})SR_{11}$, $NR_{10}C(=NR_{15})NR_8R_9$, $NR_{10}C(=CR_{14}R_{24})SR_{11}$, $NR_{10}C(=CR_{14}R_{24})NR_8R_9$, $NR_{10}C(O)C(O)NR_8R_9$, $NR_{10}C(O)C(O)OR_{10}$, $C(=NR_{13})NR_8R_9$, $C(=NOR_{13})NR_8R_9$, $C(=NR_{13})ZR_{11}$, $OC(Z)NR_8R_9$, $NR_{10}S(O)_2CF_3$, $NR_{10}C(Z)OR_{10}$, 5-($R_{18}$)-1,2,4-oxadizaol-3-yl or 4-($R_{12}$)-5-($R_{18}R_{19}$)-4,5-dihydro-1,2,4-oxadiazol-3-yl; provided that when $Y_2$ is $CO_2R_8$ or $C(Z)NR_8R_9$, then n is 0;
$R_5$ is hydrogen, $C_{1-4}$ alkyl, $C_{2-4}$ alkenyl, $C_{2-4}$ alkynyl or $NR_7R_{17}$, with the provisio that —$SR_5$ is not —$SNR_7R_{17}$ and —$SOR_5$ is not —SOH;

$R_6$ is $C_{1-4}$ alkyl, halo-substituted-$C_{1-4}$ alkyl, $C_{2-4}$ alkenyl, $C_{2-4}$ alkynyl or $C_{3-5}$ cycloalkyl;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{22}$;

$R_8$ is hydrogen, heterocyclyl, heterocyclylalkyl or $R_{11}$;

$R_9$ is hydrogen, $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl, heteroaryl or heteroarylalkyl or $R_8$ and $R_9$ may together with the nitrogen to which they are attached form a heterocyclic ring of 5 to 7 members which ring optionally contains an additional heteroatom selected from oxygen, sulfur or $NR_{12}$;

$R_{10}$ and $R_{20}$ is each independently selected from hydrogen or $C_{1-4}$ alkyl;

$R_{11}$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl, heteroaryl or heteroarylalkyl;

$R_{12}$ is hydrogen, —C(Z)$R_{13}$ or optionally substituted $C_{1-4}$ alkyl, optionally substituted aryl or optionally substituted aryl-$C_{1-4}$ alkyl;

$R_{13}$ is hydrogen, $C_{1-10}$ alkyl, cycloalkyl, heterocyclyl, aryl, arylalkyl, heteroaryl or heteroarylalkyl;

$R_{14}$ and $R_{24}$ is each independently selected from hydrogen, alkyl, nitro or cyano;

$R_{15}$ is hydrogen, cyano, $C_{1-4}$ alkyl, $C_{3-7}$ cycloalkyl or aryl;

$R_{16}$ and $R_{26}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_{12}$;

$R_{18}$ and $R_{19}$ is each independently selected from hydrogen, $C_{1-4}$ alkyl, substituted alkyl, optionally substituted aryl, optionally substituted arylalkyl or together $R_{18}$ and $R_{19}$ denote a oxygen or sulfur;

$R_{21}$ is hydrogen, a pharmaceutically acceptable cation, $C_{1-10}$ alkyl, $C_{3-7}$ cycloalkyl, aryl, aryl $C_{1-4}$ alkyl, heteroaryl, heteroarylalkyl, heterocyclyl, aroyl, or $C_{1-10}$ alkanoyl;

$R_{22}$ is $R_{10}$ or C(Z)—$C_{1-4}$ alkyl;

$R_{23}$ is $C_{1-4}$ alkyl, halo-substituted-$C_{1-4}$ alkyl, or $C_{3-5}$ cycloalkyl;

$R_{36}$ is hydrogen or $R_{23}$;

or a pharmaceutically acceptable salt thereof.

2. The compound according to claim 1 wherein $R_1$ or $R_2$ is a substituted 4-pyridyl.

3. The compound according to claim 1 wherein the substituent is $C_{1-4}$ alkyl or $NR_{10}R_{20}$.

4. The compound according to claim 1 wherein $R_1$ or $R_2$ is an optionally substituted phenyl.

5. The compound according to claim 4 wherein one or more of the optional substituents are independently selected from halogen or methoxy.

6. The compound according to claim 1 wherein $R_3$ is hydrogen, $(CR_{10}R_{20})_n(Y_2)_p$, or $(CR_{10}R_{20})_nCH_3$; and $Y_2$ is —$NR_8R_9$ or —$NR_{10}C(Z)R_8$.

7. The compound according to claim 5 wherein $R_3$ is hydrogen, methyl, amino, or —$NR_{10}C(O)R_8$.

8. The compound according to claim 1 which is:
5-(3-Methoxyphenyl)-2-methyl-4-(4-pyridyl)oxazole;
5-(4-Fluorophenyl)-2-methyl-4-(4-pyridyl)oxazole;
2-Methyl-4-(Phenyl)-5-(4-pyridyl)oxazole;
4-(4-Fluorophenyl)-2-methyl-5-(4-pyridyl)oxazole;
2-Amino-4-(4-fluorophenyl)-5-(4-pyridyl)oxazole;
4-(4-Fluorophenyl)-5-(4-pyridyl)oxazole;
4-(4-Fluorophenyl)-5-(2-methylpyrid-4-yl)oxazole;
4-(3,4-Dichlorophenyl)-5-(4-pyridyl)oxazole;
4-(3-Chlorophenyl)-5-(4-pyridyl)oxazole;
2-Acetamido-4-(4-fluorophenyl)-5-(4-pyridyl)oxazole;
or a pharmaceutically acceptable salt thereof.

9. A pharmaceutical composition comprising a pharmaceutically acceptable carrier or diluent and a compound according to claim 1.

10. A method of treating a cytokine mediated disease in an animal in need thereof which method comprises administering to said animal an effective cytokine mediating amount of a compound according to claim 1.

11. The method according to claim 10 wherein the cytokine mediated disease is asthma, adult respiratory distress syndrome, stroke, bone reasorption diseases, or arthritic joint conditions.

12. The method according to claim 10 wherein the compound is
5-(3-Methoxyphenyl)-2-methyl-4-(4-pyridyl)oxazole;
5-(4-Fluorophenyl)-2-methyl-4-(4-pyridyl)oxazole;
2-Methyl-4-(Phenyl)-5-(4-pyridyl)oxazole;
4-(4-Fluorophenyl)-2-methyl-5-(4-pyridyl)oxazole;
2-Amino-4-(4-fluorophenyl)-5-(4-pyridyl)oxazole;
4-(4-Fluorophenyl)-5-(4-pyridyl)oxazole;
4-(4-Fluorophenyl)-5-(2-methylpyrid-4-yl)oxazole;
4-(3,4-Dichlorophenyl)-5-(4-pyridyl)oxazole;
4-(3-Chlorophenyl)-5-(4-pyridyl)oxazole;
2-Acetamido-4-(4-fluorophenyl)-5-(4-pyridyl)oxazole;
or a pharmaceutically acceptable salt thereof.

13. The method according to claim 11 wherein the mediation of the disease state is by Interleukin-1 (IL-1).

14. The method according to claim 11 wherein the mediation of the disease state is by Tumor Necrosis Factor (TNF).

15. A method of treating inflammation in a mammal in need thereof which comprises administering to said mammal an effective amount of a compound according to claim 1.

16. The method according to claim 11 wherein the cytokine mediated disease is arthritis, rheumatoid arthritis, rheumatoid spondylitis, osteoarthritis, traumatic arthritis, rubella arthritis, acute synovitis, gouty arthritis, gout, sepsis, septic shock, endotoxic shock, gram negative sepsis, toxic shock syndrome, diabetes, atherosclerosis, adult respiratory distress syndrome, cerebral malaria, chronic pulmonary inflammatory disease, silicosis, pulmonary sarcoisosis, bone resorption diseases, reperfusion injury, thrombosis, glomerulonepthritis, stroke, graft vs. host reaction, allograft rejections, fever and myalgias due to infection, cachexia secondary to infection or malignancy, cachexia secondary to acquired immune deficiency syndrome, keloid formation, scar tissue formation, eczema, psoriasis, Crohn's disease, inflammatory bowel disease, ulcerative colitis or pyresis.

* * * * *